United States Patent
Lieberman et al.

(12) 
(10) Patent No.: US 9,347,089 B2
(45) Date of Patent: May 24, 2016

(54) THERAPEUTIC AND DIAGNOSTIC STRATEGIES

(75) Inventors: Judy Lieberman, Brookline, MA (US); Ashish Lal, Brookline, MA (US); Dipanjan Chowdhury, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/063,155

(22) PCT Filed: Sep. 18, 2009

(86) PCT No.: PCT/US2009/057506
§ 371 (c)(1),
(2), (4) Date: Oct. 27, 2011

(87) PCT Pub. No.: WO2010/033822
PCT Pub. Date: Mar. 25, 2010

(65) Prior Publication Data
US 2012/0059043 A1    Mar. 8, 2012

Related U.S. Application Data

(60) Provisional application No. 61/098,696, filed on Sep. 19, 2008, provisional application No. 61/098,707, filed on Sep. 19, 2008.

(51) Int. Cl.
| | | |
|---|---|---|
| *C12Q 1/68* | (2006.01) |
| *A61B 5/00* | (2006.01) |
| *A61P 35/00* | (2006.01) |
| *C12N 15/11* | (2006.01) |
| *C12N 15/113* | (2010.01) |

(52) U.S. Cl.
CPC ............ *C12Q 1/6809* (2013.01); *C12N 15/111* (2013.01); *C12N 15/113* (2013.01); *C12Q 1/6806* (2013.01); *C12N 2310/141* (2013.01); *C12N 2320/11* (2013.01)

(58) Field of Classification Search
None
See application file for complete search history.

(56) References Cited

U.S. PATENT DOCUMENTS

2006/0246491 A1    11/2006    Srivastava
2008/0050744 A1*   2/2008    Brown et al. .................. 435/6

FOREIGN PATENT DOCUMENTS

| WO | 2006108718 A1 | 10/2006 |
| WO | 2006137941 A2 | 12/2006 |
| WO | 2008036765 A2 | 3/2008 |

* cited by examiner

*Primary Examiner* — Jennifer Pitrak McDonald
(74) *Attorney, Agent, or Firm* — Mintz Levin Cohn Ferris Glovsky and Popeo, P.C.; Peter F. Corless; Christopher R. Cowles

(57) ABSTRACT

The present invention encompasses the finding that microRNAs (miRNAs) regulate certain key proteins involved in DNA repair. In some embodiments, a miRNA suppresses levels and/or activity of one or more DNA repair proteins. In some such embodiments, such suppression renders cells hypersensitive to certain DNA damage agents (e.g., γ-irradiation and genotoxic drugs, among others). The present invention provides various reagents and methods associated with these findings including, among other things, strategies for treating cell proliferative disorders, certain diagnostic systems, etc.

9 Claims, 14 Drawing Sheets

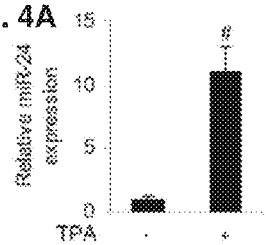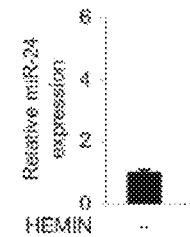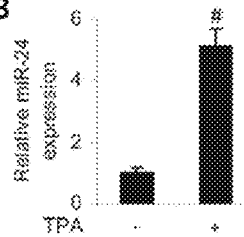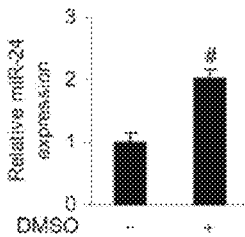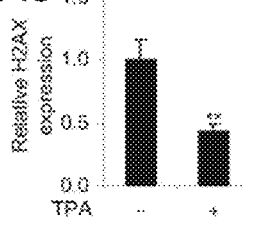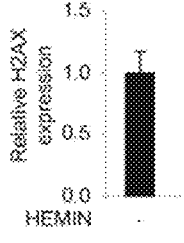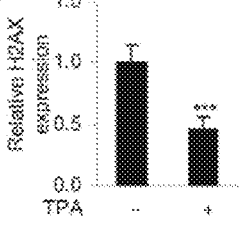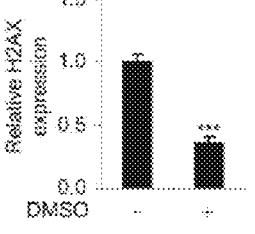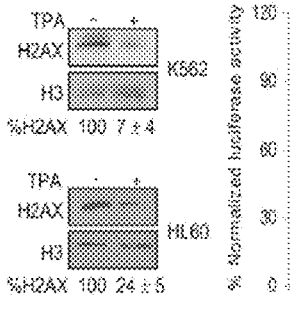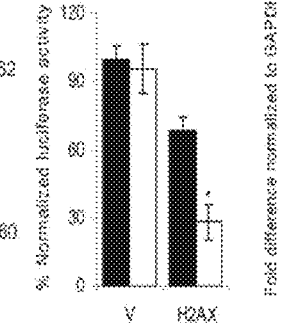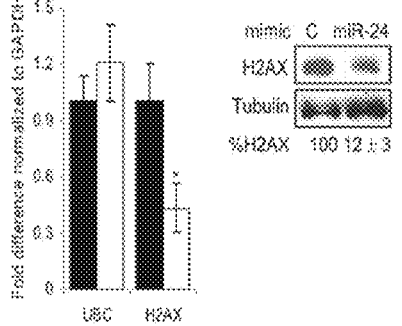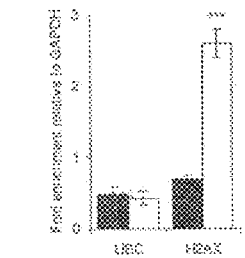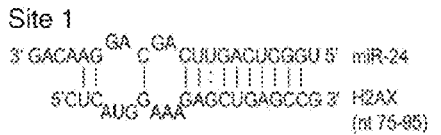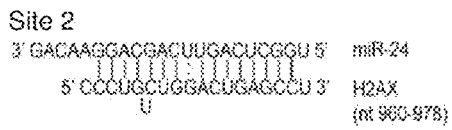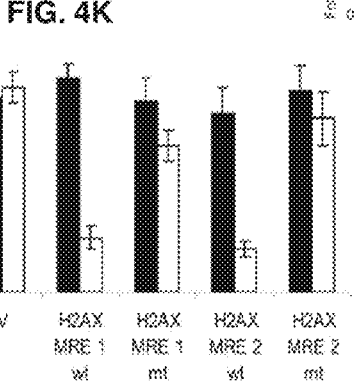

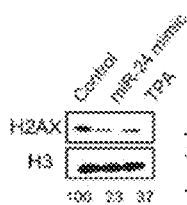
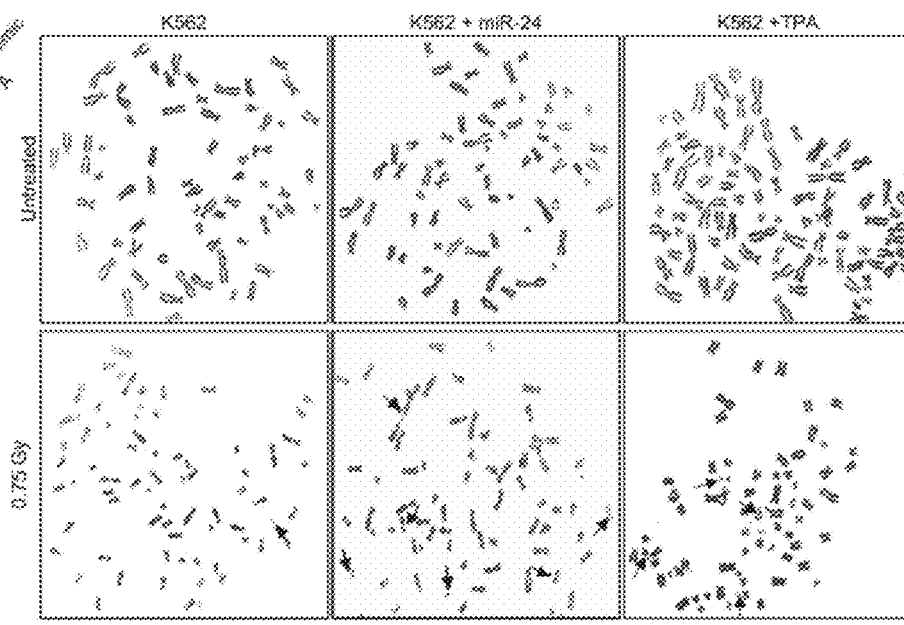
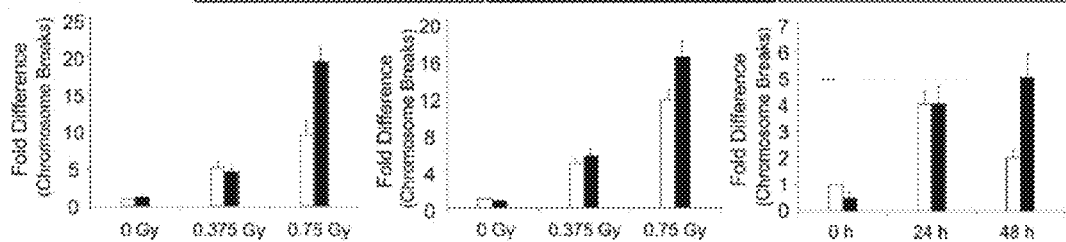
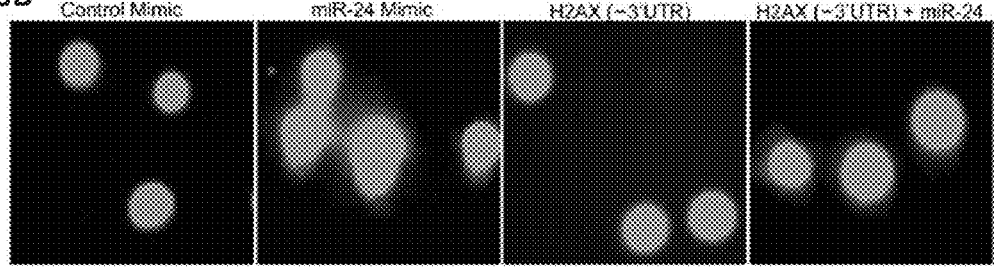
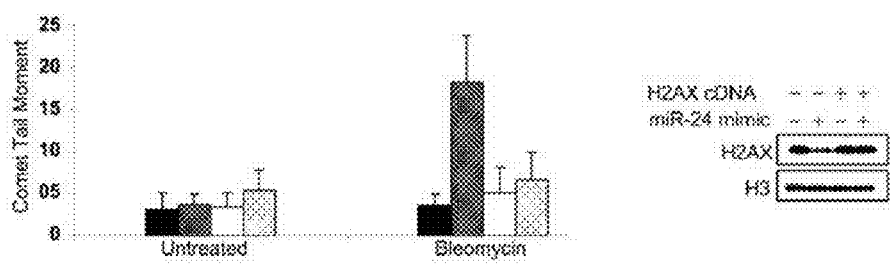

FIG. 14

Supplemental Table 1  Primers used for qRT-PCR

| Gene | Forward Primer | Reverse Primer |
|---|---|---|
| GAPD | TGCACCACCAACTGCTTAGC | GGCATGGACTGTGGTCATGAG |
| UBC | ATTTGGGTC GCGGTTCTTG | TGCCTTGACATTCTCGATGGT |
| H2AX (3'UTR) | AGCAAACTCAACTCGGCAAT | ACTCCCCAATGCCTAAGGTT |
| H2AX (coding) | GGCCTCCAGTTCCCAGTG | TCAGCGGTGAGGTACTCCAG |

Supplemental Table 2  Mutations introduced in miR-24 binding sites in H2AX-3'UTR

| GENE | MRE | Location | |
|---|---|---|---|
| H2AX | MRE(1) | 76 to 94 of H2AX 3'UTR sequence | 5' UCAUGGAAA GAGC UGAGCC 3'<br>3' GACAAGGA GACUG ... GACUGCGU 5'<br>5' UCAUGGAAAGAG GAUUAGG 3' |
| H2AX | MRE(2) | 961 to 977 of H2AX 3'UTR sequence | 5' CC UGUCUGGAC UGAGCC 3'<br>3' GACAAGGA GACUG ... GACUGCGU 5'<br>5' CC UGUCUGGA GAUUAGG 3' |

THERAPEUTIC AND DIAGNOSTIC STRATEGIES

RELATED APPLICATIONS

The present application claims the benefit under 35 U.S.C. §371 of international application serial number PCT/US2009/057506, filed Sep. 18, 2009, which claims priority under 35 U.S.C. §119 to U.S. Ser. No. 61/098,696, filed on Sep. 19, 2008, entitled "miRNA Targets", and U.S. Ser. No. 61/098,707, filed on Sep. 19, 2008, entitled "Therapeutic and Diagnostic Strategies," the entire contents of which are incorporated herein by reference.

SEQUENCE LISTING

In accordance with 37 CFR §1.52(e)(5), the present specification makes reference to a Sequence Listing (submitted electronically as a .txt file named "13063155SeqList.txt" on Oct. 27, 2011). The .txt file was generated on Oct. 27, 2011 and is 4 kb in size. The entire contents of the Sequence Listing are herein incorporated by reference.

BACKGROUND

DNA repair mechanisms are central to a variety of cellular processes, including, importantly, DNA replication and cell proliferation. Ability to influence DNA repair systems, and/or cell cycle progression generally, can provide novel therapeutic and diagnostic approaches to a variety of diseases, disorders, and conditions associated with cell proliferation (including, for example, cancer, immune-mediated disorders and/or neurodegenerative disorders).

SUMMARY

The present invention encompasses the finding that microRNAs (miRNAs) regulate certain key proteins involved in DNA repair and/or cell cycle progression. In some embodiments, a miRNA modulates levels and/or activity of one or more DNA repair and/or cell cycle progression proteins. In some such embodiments, such modulation renders cells hypersensitive to certain DNA damage agents (e.g., γ-irradiation and genotoxic drugs, among others).

The present invention specifically encompasses the finding that certain miRNAs whose expression is increased in terminally differentiated cells regulate DNA repair and/or cell cycle progression proteins. In some embodiments, the miR-NAs show increased expression in terminally differentiated hematopoietic cells. In some embodiments, the miRNAs are selected from the group consisting of miR-22, miR-125a, miR-24 (e.g., miR-24-1; miR-24-2), miR-23 (e.g., miR-23a, miR-23B), miR-27 (e.g., miR-27a, miR-27b), miR-17, miR-18, miR-19, miR-20, miR-34a, miR-92, miR-125, miR-146a, miR-155, miR-181a, 200a, miR-48, miR-84, and miR-241. In some embodiments, the miRNA is miR-24.

The present invention provides, among other things, systems for modulating DNA repair and/or cell cycle progression in cells by altering expression and/or activity of one or more such miRNAs.

The present invention provides, among other things, systems for reducing cell proliferation and/or increasing sensitivity to certain DNA damage agents through modulation of certain miRNAs and/or of miRNA-based regulation of DNA repair proteins. According to the present invention, such systems are particularly useful, for example, in reducing undesirable cell proliferation (e.g., in the context of cancer, transplant rejection, T cell immunity, etc.). In some embodiments, cells whose proliferation is to be reduced include hematopoietic cells. In some embodiments, inventive systems for reducing cell proliferation include increasing levels and/or activity of certain miRNAs in cells, such that DNA repair is reduced and/or expression and/or activity of one or more DNA repair (e.g., H2AX) or cell cycle progression proteins is altered. In some such embodiments, cells may also be exposed to one or more DNA damage agents (e.g., γ-irradiation and genotoxic drugs, among others). In some embodiments, the present invention provides systems for inducing apoptosis.

The present invention provides, among other things, systems for increasing cell proliferation and/or decreasing sensitivity to certain DNA damage agents through modulation of certain miRNAs and/or of miRNA-based regulation of DNA repair and/or cell cycle progression proteins. According to the present invention, such systems are particularly useful, for example, in cell culture applications and/or in applications where cell proliferation is desirably increased. In some embodiments, cells whose proliferation is to be increased include hematopoietic cells. In some embodiments, inventive systems for increasing cell proliferation include decreasing levels and/or activity of certain miRNAs in cells such that DNA repair is reduced and/or expression and/or activity of one or more DNA repair (e.g., H2AX) and/or cell cycle progression proteins is altered.

The present invention provides, among other things, systems for detecting cells undergoing terminal differentiation and/or cells whose DNA repair systems are compromised. Particularly useful applications of such systems, according to the present invention include, among other things, diagnostics for identifying cells and/or individuals that are particularly susceptible to DNA damage agents (e.g., γ-irradiation and genotoxic drugs, among others).

DESCRIPTION OF THE DRAWING

FIG 4A to FIG. 4K show that miR-24 down-regulates H2AX expression during terminal differentiation. miR-24, analyzed by qRT-PCR relative to U6, increases during differentiation of K562 cells (FIG. 4A) with TPA to megakaryocytes or hemin to erythrocytes (#, p<0.001, *, p<0.005) and during differentiation of HL60 cells (FIG. 4B) with TPA to macrophages or DMSO to granulocytes (#, p<0.001). HL60 cells were treated with TPA for 2 days (left panel) or DMSO for 5 days (right panel) and miR-24 levels analyzed as described above. Under the same differentiating conditions for K562 (FIG. 4C) and HL60 (FIG. 4D) cells, H2AX mRNA, normalized to GAPDH mRNA, is down-regulated (, p<0.01, K562; *, p<0.005, HL60). FIG. 4E shows that H2AX protein decreases after 2 d of TPA differentiation. Relative H2AX expression was quantified by densitometry using H3 as control. FIG. 4F shows that H2AX mRNA is selectively pulled down from K562 cell lysates with biotinylated miR-24 (white) compared to control cel-miR-67 (black). For each condition, pulled down RNA was first normalized to GAPDH mRNA in the sample and then to relative input cellular RNA (*, p<0.005). The housekeeping gene UBC was not enriched in the pull down. FIG. 4G shows a schematic representing the location of miR-24 (SEQ ID NO: 1) binding sites in the 3'UTR of H2AX mRNA (SEQ ID NOS: 2 and 3). FIG. 4H shows that miR-24 targets the 3'UTR of H2AX mRNA in a luciferase reporter assay. HepG2 cells were transfected with control miRNA (black) or synthetic miR-24 (white) for 48 hr and then with H2AX 3'UTR-luciferase reporter (H2AX) or vector (V) for 24 hr. Mean+SD, normalized to vector control, of 3 independent experiments are shown (*, p<0.001). miR-24 over-expression in HepG2 cells decreases H2AX mRNA, analyzed by qRT-PCR normalized to GAPDH (FIG. 4I; white, miR-24; black, cel-miR-67) and protein (FIG. 4J) 48 hr later. miR-24 over-expression does not alter UBC mRNA levels. In (FIG. 4A to FIG. 4D; FIG. 4F; and FIG. 4H and 4I), mean±SD are shown. FIG. 4K shows suppression of the luciferase activity of a reporter gene containing in its 3' UTR the two predicted miR-24 MRE, either wild-type (wt) or with mutated seed regions (mt). HepG2 cells were transfected with control miRNA (black) or miR-24 mimic (white) for 48 h and then with the indicated H2AX 3' UTR-luciferase reporters or vector (V). Luciferase activity was assayed 24 h later. Mean±s.d., normalized to vector control, of three independent experiments is shown. In all panels, mean±s.d. is shown.

FIG. 5A to 5D show miR-24 expression impedes DSB repair and induces chromosomal instability of γ-irradiated K562 cells. FIG. 5A shows that transfection of miR-24 mimic into K562 cells reduces H2AX comparably to TPA differentiation. H2AX was quantified relative to H3 protein by densitometry. FIG. 5B shows that representative images of metaphase chromosome spreads were prepared from treated cells 24 h after γ-irradiation. Arrows mark chromosome breaks or fragments. FIG. 5C shows chromosome breaks were quantified 24 hr after irradiation of K562 cells that were either undifferentiated (white) or had been differentiated with TPA (black, left panel) or transfected with miR-24 (black, middle panel). In the right panel, differences in chromosome breaks that were not present 24 hr following 0.375 Gy were significantly different 48 hr after irradiation in miR-24 (black) vs mock-transfected (white) cells. The mean±SD number of chromosome breaks and fragments per cell, normalized to control is plotted. FIG. 5D shows that overexpressing miR-24 increases unrepaired DSB by comet assay. K562 cells, transfected with miR-24 mimic and/or miR-24-insensitive H2AX expression plasmid, were treated or not with bleomycin (0.5 μg/ml) for 12 h and analyzed by single cell gel electrophoresis (comet assay) 12 h later. H2AX protein is compared to H3 level in the immunoblot. H2AX levels, reduced by the miR-24 mimic, are rescued by the H2AX expression plasmid. Representative images from bleomycin-treated cells are shown in the upper panel and the mean±SD comet tail moment for each condition below (black, control mimic, expression vector; dark stippled bars, miR-24 mimic, vector; white, control mimic, H2AX expression plasmid; light stippled bars, miR-24 mimic, H2AX expression plasmid). Manipulating miR-24 or H2AX levels did not affect baseline DNA damage, but DNA damage after irradiation was significantly increased (p<0.001) in miR-24 mimic-transfected cells, but only in the absence of H2AX rescue.

FIG. 6A shows that K562 cells overexpressing miR-24 (left) or treated with TPA (right) are hypersensitive to bleomycin, assessed by viability relative to mock-treated cells (□) 2 d later. TPA treatment (u) or transfection with miR-24 mimic (m), but not miR-328 mimic (FIG. 6A), significantly sensitizes K562 cells to DNA damage (p<0.005). FIG. 6B shows similarly that HepG2 cells overexpressing miR-24 (■) are hypersensitive, compared to mock-transfected cells (□) to bleomycin (left) and cisplatin (right). miR-24 over-expression significantly reduces viability to both genotoxic agents (p<0.004). miR-24-mediated hypersensitivity of K562 (FIG. 6C) and HepG2 (FIG. 6D) cells is rescued by expression of miR-24-insensitive H2AX. Cells were mock transfected (E1) or transfected with miR-24 mimic (u) or H2AX cDNA lacking the 3'UTR (FIG. 6A) or both (•). Cell viability was assayed 2 d after exposure to DNA damage and depicted relative to that of undamaged cells. Immunoblots demonstrate miR-24-mediated decrease in H2AX protein and rescue by transfecting the H2AX cDNA (no 3'UTR).

FIG. 7A shows that miR-24 knockdown in K562 cells, treated or not with TPA, specifically decreases miR-24 levels, assayed by qRT-PCR in cells transfected with miR-24 ASO relative to control ASO (Ctl). miR-24 expression in ASO-treated cells, relative to U6 snRNA, is normalized to that in control ASO-treated cells. FIG. 7B shows that miR-24 ASO enhances H2AX transcript (left) and protein levels (right) in K562 cells treated with TPA, but not in untreated, K562 cells. FIG. 7C shows that relative to untreated cells (□), TPA treatment (•) sensitizes K562 cells to bleomycin treatment. Transfection of miR-24 ASO significantly blocks bleomycin-induced apoptosis of TPA-treated K562 cells (•, p<0.003), but does not affect apoptosis of untreated K562 cells (FIG. 7A). FIG. 7D shows that transfection of miR-24 significantly enhances repair of bleomycin-induced DNA damage, as measured by comet assay, in TPA-treated K562 cells (*, P o 0.001). Representative images from bleomycin-treated cells are shown on the left and the mean±s.d. comet tail moments of three independent experiments are shown on the right.

FIG. 8§A to FIG. 8C shows that inhibition of miR-24 leads to increased cell proliferation, while miR-24 over-expression leads to cell-cycle arrest.

FIG. 10A shows that miR-24, analyzed by qRT-PCR relative to U6, increases during TPA-induced differentiation of HL60 cells to macrophages, and this increased miR-24 expression is also observed in primary human peripheral blood macrophages and granulocytes. FIG. 10B shows that H2AX mRNA (normalized to UBC mRNA), and protein (normalized to histone H3) is down-regulated during differentiation of HL60 cells and is comparable to levels in primary human peripheral blood macrophages and granulocytes.

FIG. 4 FIG. 13 shows that miR-24 is upregulated during hematopoietic cell differentiation into multiple lineages. Heat map for miRNA expression in HL60 and K562 cells differentiated into four different nondividing cell lineages, showing single-linkage hierarchical clustering, using Pearson squared as a distance metric. miRNA expression in each lane is analyzed relative to expression in control undifferentiated cells. The highlighted cluster shows miRNAs with similar expression profiles. Range is from five-fold down-regulation (green) to five-fold upregulation (red). Arrows indicate miR-24 cluster miRNAs.

FIG. 14 presents Supplemental Table 1, Primers used for qRT-PCR (SEQ ID NOS: 4-11), and Supplemental Table 2, Mutations introduced in miR-24 (SEQ ID NO: 1) binding sites in H2AX-3'UTR (SEQ ID NOS: 12-15).

DEFINITIONS

Figure 1A:
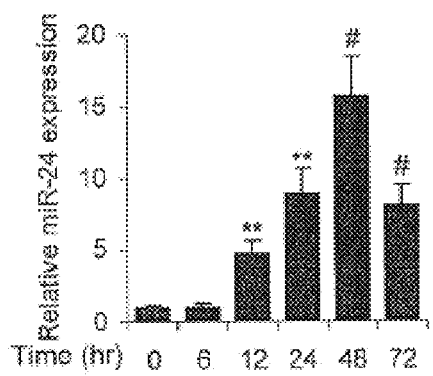
FIG. 1A to FIG. 1D show kinetics of miR-24 and H2AX transcript levels in TPA-treated K562 and HL60 cells. TPA treatment of K562 cells (FIGS. 1A, 1C) and HL60 cells (FIGS. 1B, 1D) increases miR-24 levels (FIGS. 1A, 1B) with a concurrent decrease in H2AX mRNA (1C, 1D).
Figure 1B:
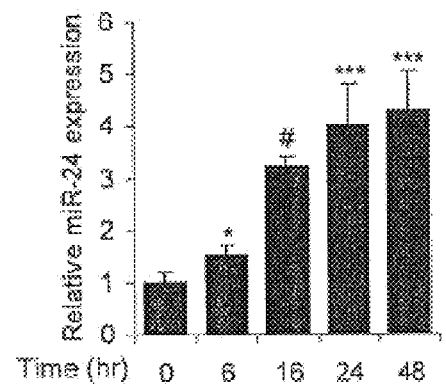
Figure 1C:
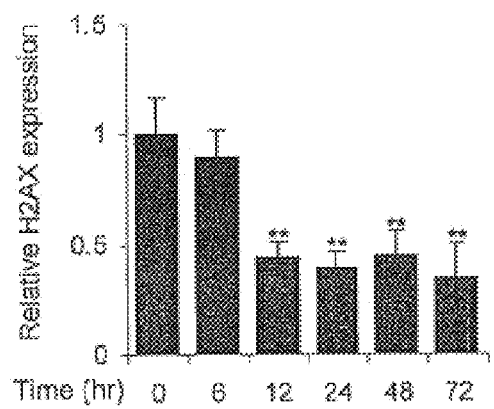
Figure 1D:
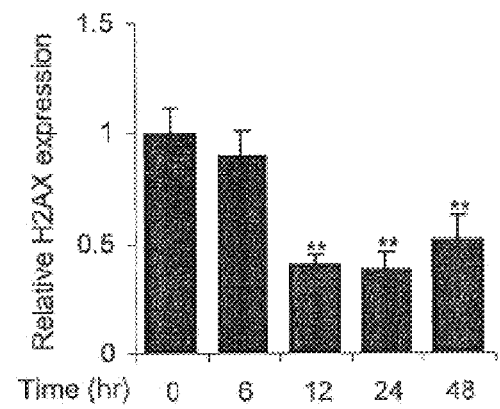

Cell Proliferative Disorder, Disease, or Condition: The term "cell proliferative disease or condition" is meant to refer to any condition characterized by aberrant cell growth, in some embodiments abnormally increased cellular proliferation.

Combination Therapy: The term "combination therapy", as used herein, refers to those situations in which two or more different pharmaceutical agents are administered in overlapping regimens so that the subject is simultaneously exposed to both agents.

DNA Damage Agents: The term "DNA damage agents", as used herein, refer to agents that, when applied to cells, damage DNA in the cells. In some embodiments, DNA damage agents are teratogens. As described herein, the present invention establishes that presence and/or activity of certain miRNAs in cells renders those cells hypersensitive to DNA damage agents. Representative such DNA damage agents include, but are not limited to, γ-irradiation, genotoxic drugs, etc.

Dosing Regimen: A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

Hypersensitive: The term "hypersensitive", is used herein to refer to cells that are more sensitive than control cells. In some embodiments, a cell is considered to be "hypersensitive" as compared with a relevant control if it shows at least about 1.2, 1.3, 1.4, 1.5, 1.6, 1.7, 1.8, 1.9, 2, 3, 4, 5, 6, 7, 8, 9, 10, 15, 20, 25, 30, 25, 40, 25, 50, 55, 60, 65, 70, 75, 80, 85, 90, 95, 100, 200, 300, 400, 500, 600, 700, 800, 900, 1000 fold or more susceptible to a particular agent or treatment.

Initiation: As used herein, the term "initiation" when applied to a dosing regimen can be used to refer to a first administration of a pharmaceutical agent to a subject who has not previously received the pharmaceutical agent. Alternatively or additionally, the term "initiation" can be used to refer to administration of a particular unit dose of a pharmaceutical agent during therapy of a patient.

MicroRNA Agent: A "microRNA agent" as that term is used herein, refers to an entity whose nucleotide sequence is substantially identical to that of a natural miRNA. As will be appreciated by those of ordinary skill in the art, naturally-occurring miRNAs are comprised of RNA. As will be further appreciated by those of ordinary skill in the art, RNA is a particularly labile chemical. Furthermore, a variety of strategies are known for preparing molecules that are structural mimics of RNA (and therefore have a "sequence" in the same sense as RNA) but that may, for example, have greater stability and/or somewhat altered hybridization characteristics. For example, in some embodiments, such structural mimics include one or more backbone modifications (e.g., substitution of phosphorothioate backbone structures for phosphodiester structures found in RNA) and/or one or more base modifications (e.g., 2'-OMe modifications). In some embodiments, such structural mimics are encompassed within "microRNA agent" as that term is used herein.

Pharmaceutical agent: As used herein, the phrase "pharmaceutical agent" refers to any agent that, when administered to a subject, has a therapeutic effect and/or elicits a desired biological and/or pharmacological effect.

Pharmaceutically acceptable carrier or excipient: As used herein, the term "pharmaceutically acceptable carrier or excipient" means a non-toxic, inert solid, semi-solid or liquid filler, diluent, encapsulating material or formulation auxiliary of any type.

Pharmaceutically acceptable ester: As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutically acceptable prodrug: The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Substantially identical: The term "substantially identical" is used to refer to a nucleic acid sequence that is sufficiently duplicative of a reference sequence to share functional attributes of the reference sequence. In particular, a sequence that is "substantially identical" to a reference sequence hybridizes to the complement of the reference sequence. In some embodiments, a sequence is "substantially identical" to a reference sequence if it shows at least 85%, 90%, 91%, 92%, 93%, 94%, 95%, 96%, 97%, 98%, 99% or more identity to the reference sequence. In some embodiments, a sequence is "substantially identical" to a reference sequence if it shows 100% identity to the reference sequence (i.e., is identical to the reference sequence).

Susceptible to: The term "susceptible to" is used herein to refer to an individual having higher risk (typically based on genetic predisposition, environmental factors, personal history, or combinations thereof) of developing a particular disease or disorder, or symptoms thereof, than is observed in the general population.

Prevention: The term "prevention", as used herein, refers to a delay in onset and/or a reduction in severity of one or more symptoms or attributes of a disease, disorder or condition, which delay or reduction is observed when a pharmaceutical agent is administered prior to onset of the symptom(s) or attribute(s).

Therapeutically effective amount: The term "therapeutically effective amount" of a pharmaceutical agent or combination of agents is intended to refer to an amount of agent(s) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

Treatment: As used herein, the term "treatment" (also "treat" or "treating") refers to any administration of a pharmaceutical agent that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Unit dose: The term "unit dose", as used herein, refers to a discrete administration of a pharmaceutical agent, typically in the context of a dosing regiment.

DESCRIPTION OF CERTAIN EMBODIMENTS

The present invention encompasses the finding that microRNAs (miRNAs) regulate certain key proteins involved in DNA repair and/or cell cycle progression. In some embodiments, a miRNA modulates levels and/or activity of one or more DNA repair and/or cell cycle progression proteins (e.g., in some embodiments, a miRNA suppresses levels and/or activity of one or more DNA repair and/or cell cycle progression proteins). In some such embodiments, such modulation renders cells hypersensitive to certain DNA damage agents (e.g., γ-irradiation and genotoxic drugs, among others).

MicroRNAs

The present invention relates to miRNAs, and particularly to miRNAs that regulate certain proteins involved in DNA repair and/or cell cycle progression. In some embodiments, relevant miRNAs are ones whose expression level increases or decreases during a particular developmental stage of interest or in response to a particular trigger or event of interest. In some embodiments, relevant miRNAs are ones whose expression and/or activity levels change during terminal differentiation of cells; in some embodiments, relevant miRNAs are up-regulated in terminally-differentiated cells. In some embodiments, relevant miRNAs are up-regulated during terminal differentiation of hematopoietic cells.

In some embodiments, relevant miRNAs are ones whose expression changes during a particular developmental stage of interest, or in response to a particular trigger or event of interest, by an amount that is about 2, 3, 4, 5, 6, 7, 8, 9, 10, 20, 30, 40, 50, 60, 70, 80, 90, or 100 fold or more.

In some embodiments, relevant miRNAs are ones that regulate cell cycle progression. In some embodiments, a relevant miRNA suppresses the expression of cell cycle regulator genes. In some embodiments, a relevant miRNA is characterized in that its overexpression increases the number of cells in the G1 phase; in some embodiments, a relevant miRNA is characterized in that its inhibition causes differentiating cells to keep proliferating.

In some embodiments, a relevant miRNA targets genes that initiate pathways such as synthesis of DNA building blocks; DNA replication; DNA damage recognition; expression, transcriptional regulation, and/or post-translational modification of cyclins, cyclin-dependent kinases, and/or other cell cycle regulators. In some embodiments, the miRNA targets MYC, E2F, and/or their targets.

In some embodiments, a relevant miRNA targets genes that are implicated in progression through the cell cycle, for example, through G1, the G1/S checkpoint, S, and/or G2/M. In some embodiments, a relevant miRNA targets genes that are involved in DNA repair, including for example, genes (e.g., H2AX) that sensitize cells to DNA damaging agents. In some embodiments, a combination of miRNA targets is used. In some embodiments, an miRNA targets a gene that promotes cell proliferation. In some embodiments, an miRNA targets a gene that suppresses cell proliferation (e.g., contributes to blocking cell cycle progression). In some embodiments, an miRNA targets a gene that participates in DNA repair. In some embodiments, an miRNA targets a gene that suppresses DNA repair.

In some embodiments, a relevant miRNA is selected from the group consisting of miR-24 and/or other miRNAs in the same cluster. In some embodiments, a relevant miRNA is miR-22 or miR-125a. For example, in some embodiments, a relevant miRNA is selected from the group consisting of miR-24 (e.g., miR-24-1; miR-24-2), miR-23 (e.g., miR-23a, miR-23B), and miR-27 (e.g., miR-27a, miR-27b), etc. In some embodiments, a relevant miRNA is a member of the let-7 family of miRNAs. In some embodiments, a relevant miRNA is selected from the group consisting of miR-48, miR-84, and miR-241. In some embodiments, a relevant miRNA is selected from the group consisting of miR-17, miR-18, miR-19, miR-20, miR-34a, miR-92, miR-125, miR-146a, miR-155, miR-181a, 200a. In some embodiments, a relevant miRNA is one that is found on chromosome 9, or on chromosome 19. In some embodiments, a relevant miRNA is one that is found in an intergenic region of a chromosome (e.g., chromosome 19). In some embodiments, a relevant miRNA is a viral miRNA. In some embodiments, a relevant miRNA is a member of the Herpes virus family. In some embodiments, a relevant miRNA is miR-K12-11. The present Examples exemplify the invention with respect to miR-24.

Among other things, the present invention provides methods that involve increasing levels and/or activities of one or more miRNAs, and particularly of one or more miRNAs that regulates DNA repair and/or cell cycle progression. Some such methods involve increasing levels of an miRNA agent, in cells. Any of a variety of strategies may be used to increase levels of an miRNA agent in cells, including, for example, introducing an miRNA agent into cells (e.g., by transfection, transformation, injection, induction, expression from a viral or other vector, etc.).

Alternatively or additionally, the present invention provides methods that involve decreasing levels and/or activities of one or more miRNAs, and particularly of one or more miRNAs that regulates DNA repair and/or cell cycle progression. Some such methods involve, for example, providing a competitor agent that competes with a target for interaction with the miRNA. To give but one specific example, in some embodiments, the present invention provides methods that utilize a "miRNA sponge" that contains multiple copies of an miRNA target sequence. In some embodiments, the present invention provides methods that involve introducing into a cell an agent that specifically degrades (or targets for degradation) a particular miRNA.

DNA Repair Proteins

Cells have evolved the capacity to remove or tolerate lesions in their DNA (Friedberg, 1985). The most direct mechanisms for repairing DNA are those that simply reverse damage and restore DNA to its normal structure in a single step. Cells can eliminate three types of DNA damage by chemically reversing it. Such direct reversal mechanisms are specific to the type of damage incurred and do not involve breakage of the phosphodiester backbone. In some embodiments, DNA damage can lead to formation of thymidine dimers, methylation of guanine bases, methylation of cytosine bases, and/or methylation of adenosine bases, or combinations thereof. Those of ordinary skill in the art will appreciate that a variety of agents induce DNA damage (e.g., γ-irradiation and/or administration of one or more genotoxic drugs, among others). In some embodiments, DNA repair proteins are those that are involved in direct reversal of DNA damage (e.g. photolyases and/or methyltransferases). In some embodiments, DNA repair proteins involved in the direct reversal pathway include human MGMT (Genbank Accession No. M2997 1) and other similar proteins.

A more complex mechanism, excision repair, involves incision of the DNA at the lesion site, removal of the damaged or inappropriate base(s), and resynthesis of DNA using the undamaged complementary strand as a template. This system of repair can further be categorized into base and nucleotide excision repair.

Base excision repair involves two major classes of repair enzymes, namely, N-glycosylases and AP endonucleases (Wallace, 1988; Sakumi and Sekiguchi, 1990; Doetsch and Cunningham; 1990). DNA N-glycosylases are enzymes that hydrolyze the N-glycosidic bond between the damaged base and the deoxyribose moiety, leaving behind an AP site on the DNA backbone. AP sites produced by the action of N-glycosylases are acted upon by AP endonucleases, which can make an incision either 3' to the AP site (class I AP lyase) or 5' to the AP site (class II AP endonuclease). All those enzymes shown to contain class I AP lyase activity possess an associated DNA glycosylase activity; however, not all glycosylases are AP lyases. Class II AP endonucleases are the major enzymes responsible for the repair of AP sites in DNA.

DNA glycosylases can be defined as enzymes which recognize specific DNA base modifications and catalyze the hydrolysis of the N-glycosylic bond that links a base to the deoxyribose-phosphate backbone of DNA (for review, see Sancar and Sancar, 1988; Wallace, 1988; Sakumi and Sekiguchi, 1990). This enzymatic activity results in the generation of an AP site. To date, several DNA glycosylases have been identified and are classified into two major families: 1) enzymes that possess only DNA glycosylase activity and 2) enzymes that contain both a DNA glycosylase activity and an associated class I AP lyase activity; that is, enzymes that catalyze a beta-elimination cleavage of the phosphodiester bond 3' to an AP site.

In some embodiments, the present invention relates to miRNAs that regulate certain proteins involved in DNA repair. In some embodiments, relevant DNA repair proteins include those from the base excision repair (BER) pathway, e.g., AP endonucleases such as human APE (hAPE, Genbank Accession No. M80261) and related bacterial or yeast proteins such as APN-1 (e.g., Genbank Accession No. U33625 and M33667), exonuclease III (ExoIII, xth gene, Genbank Accession No. M22592), exonuclease I (ExoI), bacterial endonuclease III (EndoIII, nth gene, Genbank Accession No. J02857), huEndoIII (Genbank Accession No. U79718), and endonuclease IV (EndoIV nfo gene Genbank Accession No. M22591). In some embodiments, relevant DNA repair proteins suitable for use in the invention include, additional BER proteins including DNA glycosylases such as, formamidopyrimidine-DNA glycosylase (FPG, Genbank Accession No. X06036), human 3-alkyladenine DNA glycosylase (HAAG, also known as human methylpurine-DNA glycosylase (hMPG, Genbank Accession No. M74905), NTG-1 (Genbank Accession No. P31378 or 171860), SCR-1 (YAL015C), SCR-2 (Genbank Accession No. YOL043C), DNA ligase I (Genbank Accession No. M36067), β-polymerase (Genbank Accession No. M13140 (human)) and 8-oxoguanine DNA glycosylase (OGG1 Genbank Accession No. U44855 (yeast); Y13479 (mouse); Y11731 (human)) In some embodiments, relevant DNA repair proteins include histone variants (e.g. H2AX) and transcription factors that regulate expression of DNA repair genes (e.g. XBP1). In some embodiments, the present invention relates to H2AX.

Cell Cycle Progression Proteins

The sequence of cell cycle events is rigorously controlled at specific checkpoints to ensure that each discrete stage in the cell cycle has been completed before the next is initiated. Human diseases associated with abnormal cell proliferation, including cancer, result when these rigorous controls on cell cycle progression are perturbed. On the other hand, it is also sometimes desirable to enhance proliferation of cells in a controlled manner. For example, proliferation of cells is useful in wound healing and where growth of tissue is desirable. Those of ordinary skill in the art will appreciate that there may be several mechanisms for cell cycle progression, for example the processes of mitosis and/or meiosis.

In general, cell cycle progression is regulated by a variety of cellular factors. For example, two relevant classes of cell cycle progression regulatory molecules include cyclins and cyclin-dependent kinases (CDKs). In some embodiments, cell cycle progression proteins are selected from the group consisting of cyclin D, cyclin dependent kinase 4 (CDK4), retinoblastoma susceptibility protein (RB), E2F, cyclin E, cyclin A, DNA polymerase, thymidine kinase, cyclin dependent kinase 2, cyclin B. In some embodiments, cell cycle progression proteins prevent the progression of the cell cycle. In some embodiments, for example, cell cycle progression proteins are selected from the group consisting of p21, p27, p57, p53, myc, TGFb, p16INK4a, p14arf. In some embodiments, cell cycle progression proteins are involved in DNA replication and repair checkpoints. In some embodiments, cell cycle progression proteins are selected from the group consisting of PCNA, CHEK1, BRCA1, FEN1, and UNG.

Applications

Cell Proliferative Disorders

In some embodiments, the invention provides methods and reagents for treating cell proliferative disorders, diseases or conditions. In general, cell proliferative disorders, diseases or conditions encompass a variety of conditions characterized by aberrant cell growth, preferably abnormally increased cellular proliferation. For example, cell proliferative disorders, diseases, or conditions include, but are not limited to, atherosclerosis, cancer, immune-mediated responses and diseases (e.g., transplant rejection, graft vs host disease, immune reaction to gene therapy, autoimmune diseases, pathogen-induced immune dysregulation, etc.), certain circulatory diseases, and certain neurodegenerative diseases.

In certain embodiments, the invention relates to methods and reagents for treating cancer. In general, cancer is a group of diseases which are characterized by uncontrolled growth and spread of abnormal cells. Examples of such diseases are carcinomas, sarcomas, leukemias, lymphomas and the like. In certain embodiments, the cancer is a hematological malignancy. In certain embodiments, the cancer is a solid tumor. For example, in some embodiments, the invention relates to treatment of rejection following transplantation of synthetic or organic grafting materials, cells, organs, or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; treatment of graft-versus-host disease; autoimmune diseases, such as rheumatoid arthritis, systemic lupus erythematosus, thyroiditis, Hashimoto's thyroiditis, multiple sclerosis, myasthenia gravis, type I diabetes, juvenile-onset or recent-onset diabetes mellitus, uveitis, Graves' disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treatment of infectious diseases causing aberrant immune response and/or activation, such as traumatic or pathogen induced immune dysregulation.

In some embodiments, the invention relates to treatment of any of a variety of neurodegenerative diseases such as, for example, Alzheimer's disease, Parkinson's disease, and/or Huntington's disease.

In some embodiments, the present invention provides methods of treating a cell proliferative disease, disorder, or condition, by administering to an individual who is suffering from or susceptible to the cell proliferative disease, disorder, or condition a therapeutically effective amount of an miRNA agent. In some embodiments, the therapeutically effective amount is an amount sufficient to render cells of the individual hypersensitive to one or more DNA damage agents. In some embodiments, the therapeutically effective amount is an amount sufficient to suppress expression and/or activity of one or more DNA repair proteins. In some embodiments, the therapeutically effective amount is an amount sufficient to inhibit cell proliferation. In some embodiments, the therapeutically effective amount is an amount sufficient to induce apoptosis.

In some embodiments, a cell is considered to be hypersensitive to one or more DNA damage agents if it shows increased chromosomal instability (e.g., increased numbers and/or persistence of chromosome breaks), increased cell death rates, and/or increased sensitivity to genotoxic stress.

Increasing Cell Division

In some embodiments, the present invention provides systems for increasing cell division, for example by modulating (e.g., reducing) levels and/or activities of one or more miRNAs (e.g., miR-24). In some embodiments, for example, modulation of one or more miRNA levels or activities leads to enhanced division and/or survival as compared with control cells.

In some embodiments, miRNA levels and/or activities are modulated through administration of an agent that modulates (e.g., promotes or suppresses activity of) the miRNA. To give but one specific example, in some embodiments, level and/or activity of a particular miRNA may be reduced by, for example, administration of an anti-sense agent that hybridizes with the miRNA and competes with one or more natural targets of the miRNA. In some such embodiments, the anti-sense agent is a miRNA sponge (see above).

In certain embodiments, systems for increasing cell division are useful, for example, in cell culture applications. In some embodiments, any of a variety of cell types are utilized. In some embodiments, stem cell (e.g. embryonic stem cell, hematopoietic stem cell, tissue stem cell, etc) proliferation is increased.

In some embodiments, said systems for increasing cell division are useful, for example, in the preparation and/or processing of cells or tissues for implantation. For example, in some embodiments, cells are cultured for implantation into a subject (e.g., for tissue replacement and/or repair applications).

In some embodiments, cell proliferation is increased in tissue explants.

Diagnostics

In some embodiments, the present invention provides systems for identifying cells (and/or individuals) that are suffering from or susceptible to one or more cell proliferative disorders, for example by detecting unusual levels or activities of one or more miRNAs and/or their targets (whether at the level of RNA or protein). In some embodiments, the targets include one or more DNA repair proteins.

In some embodiments, the present invention provides systems for identifying cells (and/or individuals) that are hypersensitive to DNA damage agents, for example by detecting levels or activities of one or more miRNAs and/or their targets (whether at the level of RNA or protein). In some embodiments, the targets include one or more DNA repair proteins. In some embodiments, identification of cells (and/or individuals) that are hypersensitive to DNA damage agents allows identification of cells (and/or individuals) who are suffering from or susceptible to one or more cell proliferative disorders and who are likely to benefit from therapy that includes administration of one or more DNA damaging agents or treatments (e.g., γ-irradiation and/or administration of one or more genotoxic drugs).

Pharmaceutical Compositions

Therapeutic agents (optionally including, for example, miRNA agents) may be administered to cells or individuals in accordance with the present invention, in the context of a pharmaceutical composition. In general, a pharmaceutical composition comprises at least one therapeutically active agent and at least one pharmaceutically acceptable carrier or excipient. Those of ordinary skill in the art will appreciate that a therapeutically active agent may be provided in any of a variety of forms including, for example, in a pharmaceutically acceptable salt or ester form.

Representation pharmaceutically acceptable carriers or excipients typically include, for example, one or more solvents, diluents, or other liquid vehicles, dispersion or suspension aids, surface active agents, isotonic agents, thickening or emulsifying agents, preservatives, solid binders, lubricants, permeation enhancers, solubilizing agents, and the like, as suited to the particular dosage form desired. Remington's *Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with a particular therapeutically active agent, such as by producing any undesirable biological effect or otherwise interacting in a deleterious manner with any other component(s) of the pharmaceutical composition, its use is contemplated to be within the scope of this invention.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, hydroxymethylcellulose, hydroxypropylmethylcellulose, methylcellulose, ethylcellulose, and cellulose acetate; powdered tragacanth; malt; gelatin; talc; Cremophor (polyethoxylated caster oil); Solutol (poly-oxyethylene esters of 12-hydroxystearic acid); excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

In some embodiments, a pharmaceutically acceptable carrier is selected from the group consisting of sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions; non-toxic compatible lubricants such as sodium lauryl sulfate and magnesium stearate; coloring agents; releasing agents; coating agents; sweetening, flavoring and perfuming agents; preservatives and antioxidants; and combinations thereof. In some embodiments, the pH of the ultimate pharmaceutical formulation may be adjusted with pharmaceutically acceptable acids, bases or buffers to enhance the stability of the formulated therapeutically active agent or its delivery form.

Pharmaceutical compositions may be administered in accordance with the present invention by any appropriate means including, for example, orally, parenterally, by inhalation spray, topically, rectally, nasally, buccally, vaginally or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. In many embodiments, pharmaceutical compositions are administered orally or by injection in accordance with the present invention.

Combination Therapy

In accordance with the present invention, two or more therapeutically active agents or regimens may be administered simultaneously to an individual.

To give but one example, in some embodiments, it may be desirable to administer an miRNA agent in combination with one or more DNA damage agents or treatments (e.g., γ-irradiation and/or one or more genotoxic drugs). In some embodiments, combinations of miRNA agents and DNA damage agents or treatments are administered to individuals suffering from or susceptible to one or more cell proliferation diseases, disorders, or conditions.

EXEMPLIFICATION

Materials and Methods

Cell Culture and Differentiation

HepG2 cells were grown in DMEM supplemented with 10% FCS. HL60 and K562 cells were grown in RPMI-1640 supplemented with 10% FCS. K562 cells ($0.5 \times 10^6$ cells/ml) were treated with TPA (16 nM, 2 d) or Hemin (100 μM, 4 d) for differentiation into megakaryocytes or erythrocytes, respectively. To induce macrophage or granulocyte differentiation, HL60 cells ($0.5 \times 10^6$ cells/ml) were treated with TPA (16 nM, 2 d) or DMSO (1.25%, 5 d), respectively. We isolated human polymorphonuclear neutrophils (PMN) from whole blood after removing mononuclear cells and platelets by Ficoll-Hypaque density gradient centrifugation. Erythrocytes were lysed by treatment with ice-cold isotonic lysis buffer (0.155 M NH4Cl, pH 7.4). The remaining PMN cells were washed with Hanks' balanced salt solution and suspended in RPMI medium containing 10% (v/v) FCS. We isolated human macrophages from peripheral blood as described in Song et al. 2003.

RNA Isolation and Quantitative RT-PCR

Total RNA was isolated using Trizol (Invitrogen) and reverse transcribed using random hexamers and superscript II reverse transcriptase (Invitrogen). qRT-PCR was performed in triplicate samples using the SYBR Green master mix (Applied Biosystems) and the BioRad iCycler. Primers are provided in Supplemental Table 1. Results were normalized to GAPDH. miRNA quantitative PCR was done in triplicate using the TaqMan MicroRNA Assay from Applied Biosystems as per the manufacturer's instructions and normalized to U6 SnRNA.

miRNA microarray

We performed miRNA microarrays as described in Song et al. 2003.

miRNA Mimic and Antisense Oligonucleotide Transfection

HepG2 cells ($2.5 \times 10^5$/well) were reverse transfected with 30 nM miRNA to control (cel-miR-67) mimics (Dharmacon) using NeoFx (Ambion) following the manufacturer's instructions. K562 cells were transfected with miRNA or control mimics (100 nM) using Amaxa nucleofection following the manufacturer's protocol. K562 cells were treated with TPA (16 nM, 2 d) and were transfected with 100 nM miR-24 ASO using lipofectamine 2000 (Invitrogen) and 36 h later these cells were exposed to indicated concentrations of bleomycin and cell viability was assessed 2 d later.

Biotin Pull-Down

K562 cells ($1 \times 10^6$/well) were transfected with 3'-biotinylated miR-24 (Dharmacon) or 3'-biotinylated control miRNA (cel-miR-67) at a final concentration of 100 nM in six-well plates in triplicate wells using Amaxa nucleofection following the manufacturer's protocol. Twenty-four hours later, the cells were trypsinized and pelleted at 500×g. After washing twice with PBS and resuspension in 0.5 ml lysis buffer (20 mM Tris (pH 7.5), 100 mM KCl, 5 mM $MgCl_2$, 0.3% NP-40, 50 U of RNase OUT (Invitrogen), complete mini-protease inhibitor cocktail (Roche Applied Science)), and incubation at 4° C. for 5 min, the cytoplasmic extract was isolated by centrifugation at 10,000×g for 10 min. Streptavidin-coated magnetic beads (50 μl, Invitrogen) were blocked for 2 hr at 4° C. in lysis buffer containing 1 mg/ml yeast tRNA and 1 mg/ml BSA (Ambion) and washed twice with 1 ml lysis buffer. Cytoplasmic extract was then added to the beads and incubated for 4 h at 4° C., following which the beads were washed five times with 1 ml lysis buffer. RNA bound to the beads (pull-down RNA) or from 10% of the extract (input RNA), was isolated using Trizol LS reagent (Invitrogen). The level of mRNA in the miR-24 or control pull-down was quantified by qRT-PCR and normalized to its abundance in the input RNA.

Luciferase Assay

HepG2 cells ($2.5 \times 10^5$/well) were reverse transfected in triplicate with 30 nM miR-24 mimic, miRNA-328 mimic or control miRNA mimic. Two days later, cells were transfected using Lipofectamine 2000 (Invitrogen) with psiCHECK2 (Promega) vector (0.5 μg/well) containing the 3'UTR of H2AX cloned in the multiple cloning site of Renilla luciferase or control. After 24 hr luciferase activities were measured using the Dual Luciferase Assay System (Promega) and TopCount NXT microplate reader (Perkin Elmer) per manufacturer's instructions. Data were normalized to Firefly luciferase. To test whether H2AX mRNA is directly regulated by miR-24, we cloned the two predicted MREs in the H2AX 3' UTR into the multiple cloning site of psiCHECK2 and also the mutant versions that disrupted base-pairing between the binding sites and miR-24. HepG2 cells were cotransfected with these plasmids and miR-24 or control mimics for 48 h using Lipofectamine 2000, before we performed the luciferase assays as described above.

Immunoblot

K562 cells ($1 \times 10^6$) were transfected with miR-24 mimics or control miRNA mimics (cel-miR-67) as above and 48 h later whole cell lysates were prepared using RIPA buffer (150 mM NaCl, 1% NP-40, 0.5% sodium deoxycholate, 0.1% SDS, 50 mM Tris, pH 8.0). Protein samples were quantified using Bradford reagent (BioRad) and resolved on 10% SDS-PAGE gels and analyzed by immunoblot probed with antibodies to H2AX (Upstate Biotech), CHEK1 (cell Signaling), histone H3 (Cell Signaling), tubulin (Sigma). All antibodies were used at a dilution of 1:1000.

Chromosome Breakage Analysis

K562 and HepG2 cultures were exposed in duplicate wells to indicated doses of γ-irradiation and incubated at 37° C. for indicated times in 5% $CO_2$. Cells were harvested and processed for chromosomal analysis following standard methods (S1). 50-75 Wright-stained metaphases for each condition were scored for chromosomal aberrations.

Single Cell Gel Electrophoresis (Comet) Assay

Single cell comet assays were performed as per manufacturer's instructions (Trevigen). Briefly, cells were transfected with siRNAs and 60 h later DSBs induced with CPT (2 μM, 1 h, 37° C.). Treated or untreated cells were collected, resuspended in ice cold PBS at $10^5$ cells/ml, mixed with low-melt agarose (1:10 ratio) and spread on frosted glass slides. After the agarose solidified, the slides were successively placed in lysis and alkaline solutions (Trevigen). Slides were then subjected to electrophoresis (1V/cm distance between electrodes) for 10 min in 1×TBE buffer and cells were fixed with 70% ethanol and stained with SYBR Green. Nuclei were visualized using epifluorescent illumination on a Zeiss microscope and images analyzed with the NIH Image program. DNA damage was quantified for 75 cells for each experimental condition by determining the tail moment, a function of both the tail length and intensity of DNA in the tail relative to the total DNA, using the software Comet Score (TriTek). Statistical analysis was by Student's t-test.

Cell Viability Assay microRNA-transfected K562 or HepG2 cells were seeded ($2\times10^3$ cells/100 µl) into octuplicate microtiter wells, incubated overnight, and then treated with indicated reagents or medium for 48 h. Viability was measured by CyQuant Cell Proliferation Assay Kit as per manufacturer's instructions (Molecular Probes). Results were expressed as $OD_{520}$ relative to that of untreated cells.

Results

Once a cell has terminally differentiated and no longer replicates its DNA, its need to repair DNA damage is reduced. Although ongoing DNA damage from oxidative metabolism and exogenous agents may be similar in dividing and nondividing cells, endogenous double stranded breaks (DSB) that occur during DNA replication and compromise genomic integrity are radically reduced or absent and the danger of propagating damaged chromatin in progeny cells is minimized once a cell has stopped dividing. Nonetheless, cells that do not divide need to maintain the integrity of the genes they transcribe. For some long-lived and essentially irreplaceable cells, such as neurons, DNA repair may be more essential than for short-lived cells, such as terminally differentiated blood cells. Dividing cells handle the risk of creating DSB during DNA replication by expressing and activating the homologous recombination (HR) repair machinery in a cell cycle dependent fashion only during S phase. Moreover, during cell division, DNA damage checkpoint proteins survey for unrepaired DNA damage to prevent cell cycle progression at G1/S and G2/M. As a consequence of their reduced needs for DNA repair, nondividing cells have an attenuated response to DSB (1).

The molecular mechanisms behind the down-regulation of DNA repair in terminally differentiated cells are generally not well understood. In some cases, specific repair proteins are down regulated. For instance, Chek1, the orchestrator of cell cycle arrest in response to replication mediated DNA damage in proliferating cells, is absent in terminally differentiated tissues (2). Likewise, E2F1 and p53 expression are down-regulated in terminally differentiated myotubes (3, 4). mRNA for Ku, the DNA binding proteins of the DNA-dependent protein kinase, which plays a central role in DSB repair by nonhomologous end joining (NHEJ), decreases during differentiation of HL-60 cells into monocytes (5). However, other repair pathways besides DSB repair, such as base excision repair (BER) and transcription-coupled repair, which repair lesions of equal importance in nondividing and dividing cells, may be undiminished after terminal differentiation.

The microRNA (miRNA) miR-24 is uniformly up-regulated during terminal differentiation of 2 hematopoietic leukemia cell lines, HL60 and K562, into multiple cell lineages as well as in CD8 T cell and muscle cell differentiation (accompanying manuscript, (6, 7)) (FIG. 4A and FIG. 4B). In the accompanying patent application, U.S. Ser. No. 61/098, 696, filed on Sep. 19, 2008, we developed a biochemical approach to identify the genes regulated by a miRNA by isolating mRNAs that bind to a transfected biotinylated mimic of the processed active miRNA transcript. 269 mRNAs were significantly enriched in the miR-24 pull-down. Genes involved in DNA repair and regulating cell cycle progression were highly significantly enriched in the pull down.

In particular, of the top 15 enriched gene ontology (GO) processes, 11 were involved in various aspects of cell cycle regulation and 2 were in the response to DNA damage and DNA repair. miR-24 pulled down 31 of 401 genes identified as participating in response to DNA damage (7.7%, p=7E-13) and 26 of 313 genes associated with DNA repair (8.3%, p=1E-11). Some of the key nodes in a bioinformatic analysis of the network of known direct interactions of the pulled-down gene products included PCNA, which localizes to DNA replication forks and is required to repair and resolve stalled replication forks (8); CHEK1, the checkpoint protein that is activated by ATR and induces cell cycle arrest at G2/M in response to unresolved DNA damage; BRCA1, which participates in a complex that activates DSB repair (9); FEN1, a flap endonuclease which removes the 5' ends of Okazaki fragments during lagging-strand DNA synthesis and participates in BER (10). In addition to these nodes many of the miR-24-bound genes are key players in DNA repair, including UNG, the major cellular uracil DNA glycosylase (11), EXO1, a 5'-3' exonuclease that has a key role in multiple DNA repair and replication pathways (12); H2AX, a histone variant that gets phosphorylated at DSB where it serves to stabilize checkpoint and repair factors (13); and XBP1, a transcription factor that upregulates DNA repair genes (including FEN 1 and H2AX) (14). The top 3 over-represented GO processes identified in another data set—the overlap of genes whose mRNA expression was significantly reduced by miR-24 over-expression with the set of miR-24 predicted targets by TargetScan 4.2—were DNA damage checkpoint (4 of 44 genes, 9.1%, p=0.0001), DSB repair via HR (3 of 17 genes, 17.6%, p=0.0001) and recombinational repair (3 of 17 genes, 17.6%, p=0.0001). These analyses strongly suggested that miR-24 might inhibit DNA repair, with perhaps a special emphasis on genes involved in repairing lesions that occur during DNA replication.

To identify miRNAs regulating DNA repair during terminal hematopoietic cell differentiation, we analyzed miRNA expression by microarray in two human leukemia cell lines—K562 cells differentiated to megakaryocytes using 12-O-tetradecanoylphorbol-13-acetate (TPA) or to erythrocytes with hemin, and HL60 cells differentiated to macrophages using TPA or to monocytes using vitamin D3 (FIG. 4). Only a few miRNAs were consistently upregulated (by at least 40%) in all four systems of terminal differentiation: miR-22, miR-125a and members of the two miR-24 clusters—miR-24, miR-23a, miR-23b and miR-27a. miR-24 stood out as the most upregulated miRNA. The only member of the two miR-24 clusters that was not consistently upregulated was miR-27b, whose hybridization signal was substantially lower for all conditions than the other cluster members, suggesting that hybridization to that probe was inefficient. We therefore focused our study on miR-24, which we hypothesized might regulate terminal differentiation in nondividing cells across multiple cell lineages.

We verified the microarray results by quantitative reverse transcription PCR (qRT-PCR). miR-24 was consistently upregulated during terminal differentiation of HL60 and K562 cells (FIG. 4A and FIG. 4B) and in differentiation of CD8 T cells, muscle cells and embryonic stem cells 15-17. One of the biggest challenges in studying miRNAs is to identify target genes and correlate their downregulation with cellular properties. Computational algorithms have been developed to predict putative miRNA targets based on complementarity to the 3' untranslated region (UTR) of the target message, particularly of miRNA nucleotides 2-8 (the 'seed' region) (18). These tools (TargetScan, PicTar, rna22, miRanda) predict overlapping, but distinct, miR-24 target gene sets (18). One strategy to counter this problem is to pursue targets predicted by multiple algorithms, and with a high prediction score. The DSB repair gene predicted by all algorithms with a high recognition score was H2AFX, encoding histone variant H2AX.

One of the earliest events in the DSB response is phosphorylation of H2AX at Ser139 by members of the phosphatidylinositol-3 kinase-like family of kinases (13). Phosphorylated H2AX (termed γ-H2AX) participates in DNA repair, replication, and recombination and cell cycle regulation (13). The large domains of γ-H2AX generated at each DSB can be visualized by immunostaining as nuclear foci. γ-H2AX foci bind and retain an array of cell cycle and DNA repair factors (cohesins, MDC1, Mrel 1, BRCA1, 53BP1, etc.) at the break site (15, 16). Importantly, loss of a single H2AX allele compromises genomic integrity and enhances cancer susceptibility in mice (17, 18). This observation has both clinical and mechanistic implications. The H2AX dosage effect may reflect its structural role in chromatin. H2AX comprises ~15% of cellular H2A, and there are two H2A molecules per nucleosome. Thus, H2AX should be present, on average, in about one of three nucleosomes, and this density likely is reduced in cells with less H2AX, which may interfere with H2AX function. Therefore, a subtle change in cellular H2AX, as might occur with miRNA targeting, may significantly impact DSB repair. Because of the critical role of H2AX in DNA repair and the known consequences of haploinsufficiency, we focused on validating and studying the effect of miR-24 on H2AX.

H2AX mRNA and protein declined during K562 and HL60 cell differentiation (FIG. 4C to FIG. 4E). The H2AX transcript can be processed alternatively to a B1.6-kb replication-independent transcript with a poly(A) tail or a B0.6-kb transcript found only in dividing cells, which has a short 3' UTR and lacks a poly(A) tail (19). The shorter transcript, whose sequence is not annotated, might lack miR-24 recognition sites, because the H2AX transcript without the 3' UTR is 505 bases long, leaving only about 100 bp for the 3' UTR. This H2AX transcript containing a shorter 3' UTR and expressed only in dividing cells could be an example of the recently described principle of preferential miRNA regulation of longer transcripts in nondividing cells.

To investigate whether miR-24 regulates H2AX expression, we first quantified H2AX mRNA in streptavidin pull-downs from K562 cells transfected for 24 hr with 3'-biotinylated miR-24 or control biotinylated miRNA (cel-miR-67) (FIG. 4F) (accompanying patent application U.S. Ser. No. 61/098,696, filed on Sep. 19, 2008). Capture of H2AX mRNA in the miR-24 pull-down, analyzed by qRT-PCR normalized to GAPDH, was enhanced by more than 3-fold compared to pull-down with the control miRNA. Pull-down of another housekeeping gene (UBC) did not differ from background. Unlike most of the mRNAs pulled-down by miR-24, H2AX is a predicted target of miR-24 by both TargetScan 4.2 and PicTar. Its 3'UTR, which is 1086 nucleotides long, encodes 2 evolutionarily conserved 7-mer exact matches to the miR-24 seed at positions 88-94 and 971-977 and each site has additional pairings to the 3'-region of miR-24 (FIG. 4G). PicTar predicts another conserved miRNA interaction (miR-328) with the H2AX 3'UTR.

Next, by qRT-PCR, using primers from the H2AX coding region that measure both transcripts, we found a four-fold reduction in H2AX mRNA in TPA-treated K562 cells (data not shown). Using primers specific for the longer transcript, H2AX mRNA declined by two-fold when K562 cells were differentiated by TPA to megakaryocytes or by hemin to erythrocytes, and when HL60 cells were differentiated by TPA to macrophages or by DMSO to granulocytes (FIG. 4C and FIG. 4D ). The level of H2AX protein, measured after TPA induction, dropped by 14-fold in K562 cells and 4-fold in HL60 cells (FIG. 4E). The strong decrease in H2AX protein levels (relative to the modest decrease in H2AX mRNA level) during differentiation may be attributed to miR-24-mediated translational inhibition of the residual H2AX transcripts. We first detected increased miR-24 and reduced H2AX mRNA levels in TPA-differentiated K562 and HL60 cells 12 h after adding TPA, at which time the cells had stopped dividing (FIG. 1A to FIG. 1D, and FIG. 9B). The relatively high miR-24 and low H2AX mRNA and proteins levels in vitro differentiated cells were comparable to levels in primary human peripheral blood monocytes and granulocytes (data not shown). The reduction in H2AX mRNA coincident with increased miR-24 in differentiated cell lines and primary blood cells could be due to miR-24 inhibition of H2AX mRNA expression and/or stability.

Figure 2A:
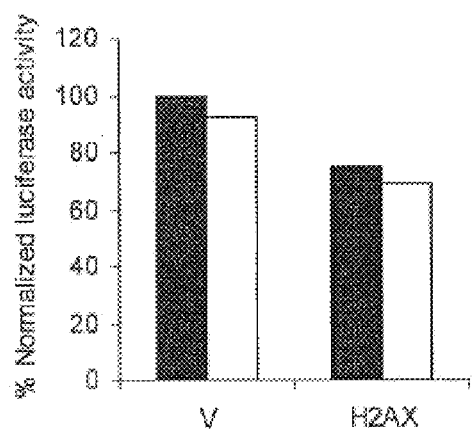
FIG. 2A and FIG. 2B demonstrate, in FIG. 2A, that miR-328 does not target the 3'UTR of H2AX mRNA in a luciferase reporter assay, where HepG2 cells were transfected with control miRNA (black) or synthetic miR-328 (white) for 48 hr and then with H2AX 3'UTR-luciferase reporter (H2AX) or vector (V) for 24 hr.; and, in FIG. 2B, that miR-328 overexpression in K562 cells has no effect on H2AX mRNA (left), analyzed by qRT-PCR normalized to GAPDH, and protein (right) 48 hr later.
Figure 2B:
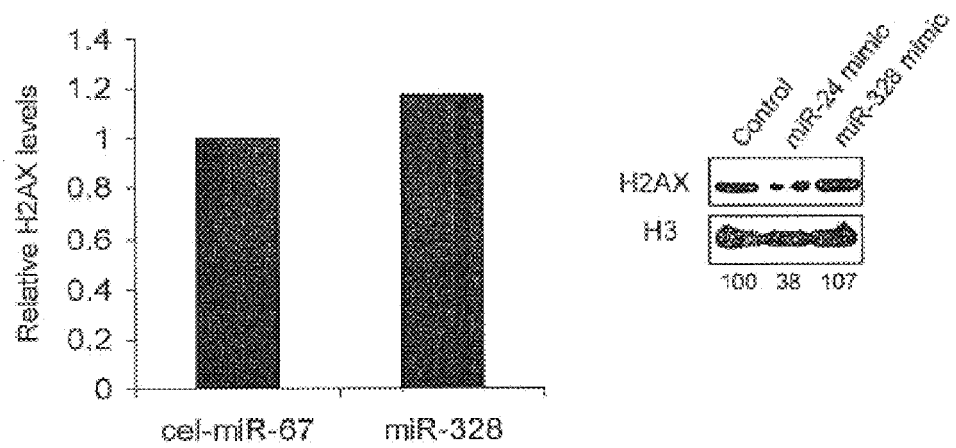

We next tested the effect of miR-24 on luciferase expression from control or H2AX 3'UTR-containing reporter genes in HepG2 cells. Luciferase activity was unchanged from control reporters, but was reduced more than 2-fold by miR-24 expression (FIG. 4H). miR-24 over-expression in HepG2 cells decreased H2AX mRNA by 2-fold, while protein expression was reduced even more (−8-fold) (FIG. 4I and FIG. 4J) Overexpressing miR-328 predicted (by PicTar) to target the 3'UTR of H2AX had no effect on luciferase activity or H2AX mRNA or protein levels, further underlining the specificity of the miR-24/H2AX interaction (FIG. 2A and FIG. 2B). Collectively, these results demonstrate that miR-24 binds to the 3'UTR of H2AX mRNA and down-regulates its expression likely by promoting both mRNA decay and inhibiting translation.

H2AX is a predicted miR-24 target by both TargetScan 4.2 and PicTar. Its 3' UTR, which is 1,086 nucleotides long, encodes two evolutionarily conserved heptamer exact matches to the miR-24 seed, at positions 88-94 and 971-977, and each site has additional pairings to the 3' region of miR-24 (FIG. 4G). PicTar predicts another conserved miRNA interaction (miR-328) with the H2AX 3' UTR. To identify the miR-24 miRNA recognition elements (MRE) in the H2AX 3' UTR, we inserted each of the predicted miR-24 MREs, as well as MREs with a mutated seed region, into the 3' UTR of luciferase reporter genes. Luciferase activity was reduced approximately four-fold when either of the wild-type miR-24 MREs was inserted, but the mutated MREs (Supplementary Table 2 of FIG. 14) had little effect (FIG. 4K). Therefore, miR-24 regulates H2AX expression by binding to the two sites predicted by TargetScan and PicTar. Although MRE2 would be found only in the longer H2AX transcript, MRE1 could potentially be present in both transcripts. The shorter transcript will need to be cloned to determine whether this is the case. Overexpressing miR-328, which is predicted (by PicTar) to target the 3' UTR of H2AX, had no effect on luciferase activity or H2AX mRNA or protein levels, further underlining the specificity of the miR-24-H2AX interaction (FIG. 2A and FIG. 2B). Collectively, these results strongly suggest that miR-24 binds to the 3' UTR of H2AX mRNA and downregulates its expression, probably by promoting both mRNA decay and inhibiting translation.

Figure 3A:
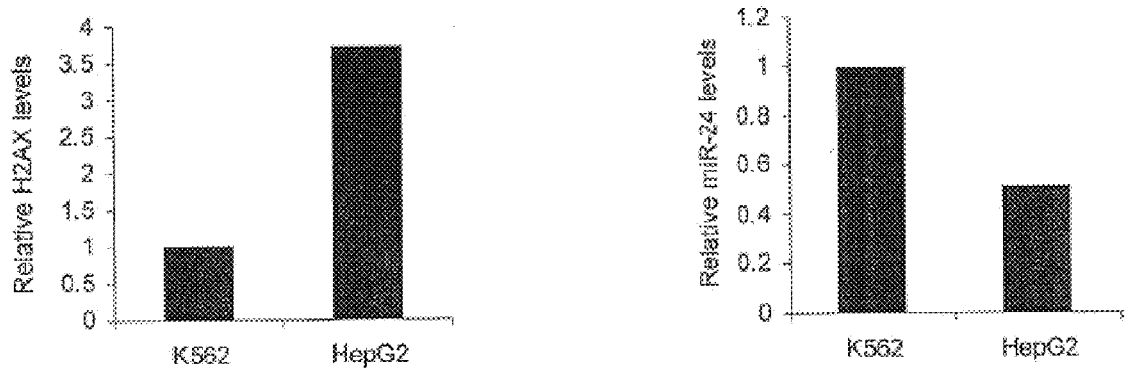
FIG. 3A to FIG. 3C show that chromosomal aberrations after γ-irradiation are greater in K562 than HepG2 cells. HepG2 cells express less miR-24 (FIG. 3A, right panel) and more H2AX (FIG. 3A, left panel) than K562 cells. Cells were either untreated or irradiated and incubated for 24 h before metaphase spreads were prepared. For each condition, at least 50 metaphase spreads were examined. The average number of cells with chromosomal aberrations (FIG. 3B) and chromosomal aberrations per cell (FIG. 3C) were analyzed. In (FIG. 3B) and (FIG. 3C) white bars represent K562 cells; black bars, HepG2 cells.
Figure 3B:
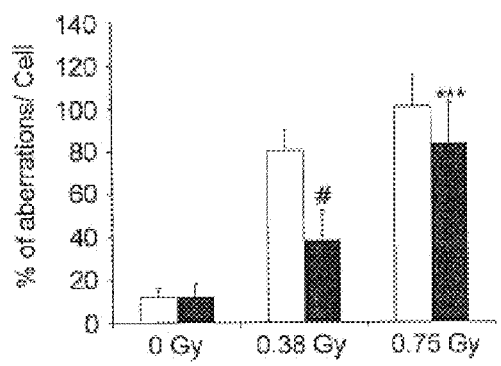
Figure 3C:
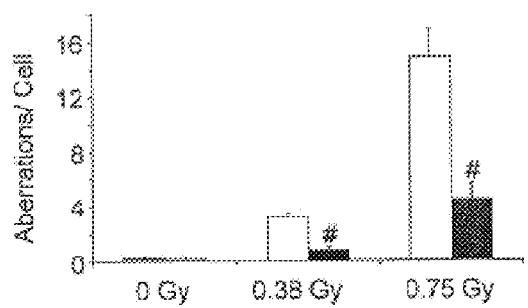

To determine whether miR-24-mediated H2AX down-regulation affects DSB repair, we first evaluated the most serious consequence of unrepaired DSB, chromosomal instability, in K562 cells that were transfected with miR-24 or mock transfected. The transfection conditions were chosen to achieve a level of H2AX knockdown similar to what is observed during TPA differentiation (FIG. 5A). Metaphase spreads were prepared 24 hr after low dose γ-irradiation (FIG. 5B). K562 cells over-expressing miR-24 had twice as many chromosome breaks and fragments as control cells after exposure to 0.75 Gy (p<0.001; FIG. 5C, left). Similarly TPA-differentiated K562 cells were significantly more sensitive to 0.75 Gy radiation than undifferentiated cells (p<0.003; FIG. 5C, middle). Although there were not significantly more breaks 24 hr after exposure to a lower dose of radiation (0.38 Gy), more chromosomal instability was seen at this dose the next day in miR-24 transfected cells (FIG. 5C, right). Undifferentiated and untransfected K562 cells, which have significantly higher endogenous expression of miR-24 and 4-fold less relative H2AX mRNA than HepG2 cells, also show more chromosomal aberrations after irradiation than HepG2 cells (FIG. 3).

As another indicator of unrepaired DNA damage, the persistence of DSB was measured by single cell gel electrophoresis (comet assay) after low dose bleomycin treatment (FIG. 5D). The comet moment quantifies the extent of unrepaired DNA damage. Although the basal comet moment was not significantly changed by miR-24 transfection, the comet tails were 5-fold higher (p<0.001) in miR-24 transfected cells compared to control miRNA-transfected cells after bleomycin treatment. To determine whether the effect of miR-24 on DSB repair was mediated via its effect on H2AX, K562 cells were co-transfected with miR-24 and a miR-24-insensitive H2AX expression plasmid without the H2AX 3'UTR. The expression plasmid fully rescued the cells; cells over-expressing miR-24 and H2AX lacking the 3'UTR had no significant increase in comet moment after bleomycin compared to cells transfected with the miRNA control and expression vector. This result strongly suggests that miR-24 regulates DSB repair by controlling H2AX.

Figure 6A:
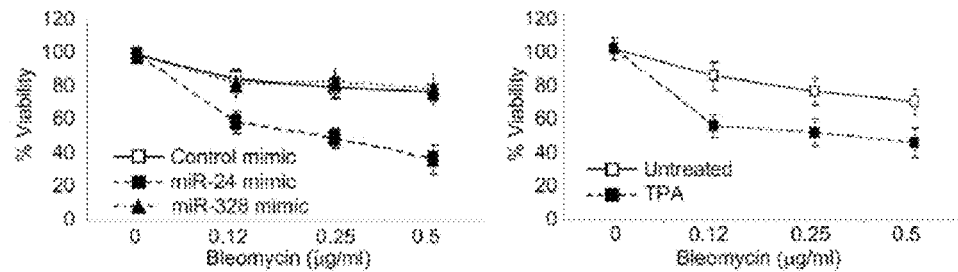
FIG. 6A to FIG. 6D shows that cells overexpressing miR-24 are hypersensitive to DNA damage by cytotoxic drugs.
Figure 6B:
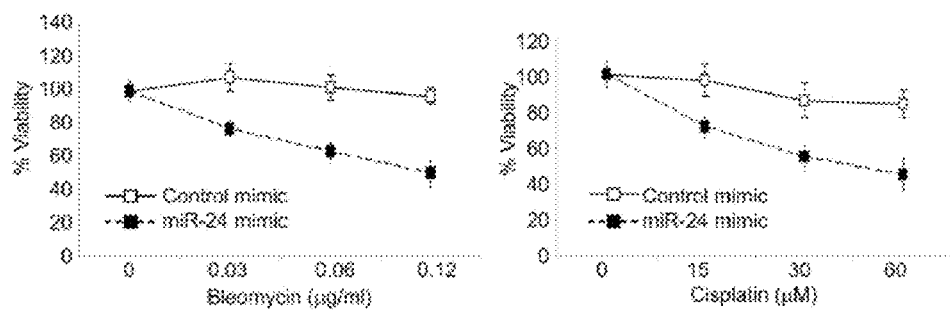
Figure 6C:
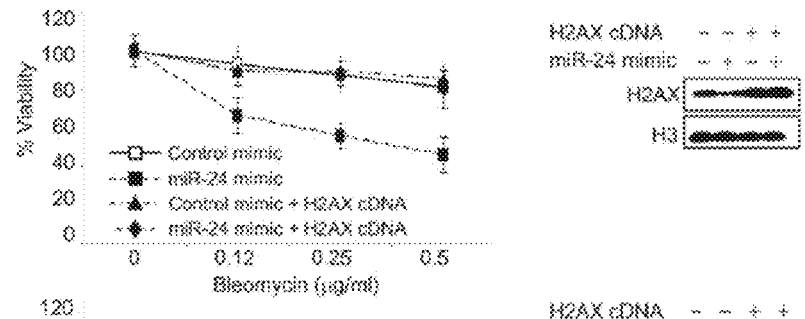
Figure 6D:
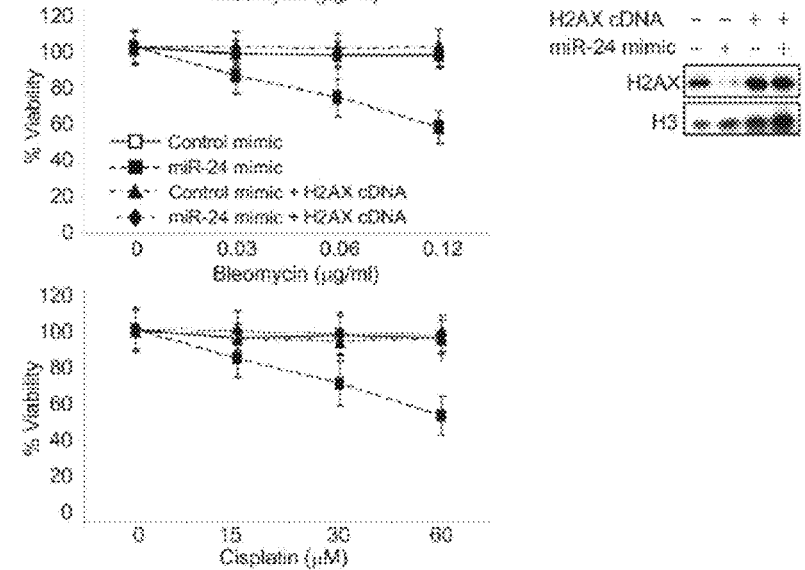

Because of impaired DNA damage repair, H2AX deficiency also leads to increased cell death after exposure to genotoxic drugs. We compared cell viability of K562 cells over-expressing miR-24, miR-328 or mock transfected after treatment with bleomycin (FIG. 6A, left). Consistent with the chromosomal breakage and comet assay analysis, cells over-expressing miR-24 were significantly hypersensitive to DNA damage as were TPA-differentiated cells relative to undifferentiated cells (FIG. 6A, right). miR-328 over-expression, however, had no effect, suggesting that miR-328 is not a physiologically relevant regulator of H2AX. We also found that unlike miR-24, transfection of miR-328 mimics does not alter H2AX protein levels in K562 cells (FIG. 2B). The effect of miR-24 on DNA damage sensitivity was further confirmed by treating miR-24 mimic-transfected HepG2 cells with bleomycin (FIG. 6B, left) and cisplatin (FIG. 6B, right). miR-24 significantly enhanced cytotoxicity caused by both drugs. The effect of miR-24 on survival was fully rescued by over-expressing miR-24-insensitive H2AX in both K562 (FIG. 6C) and HepG2 (FIG. 6D) cells. Together these results suggest that miR-24-mediated down-regulation of H2AX inhibits the DNA damage response in terminally differentiated cells.

Figure 7A:
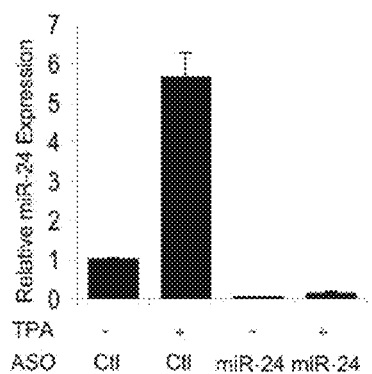
FIG. 7A to FIG. 7D shows that antagonizing miR-24 enhances cell resistance to bleomycin.
Figure 7B:
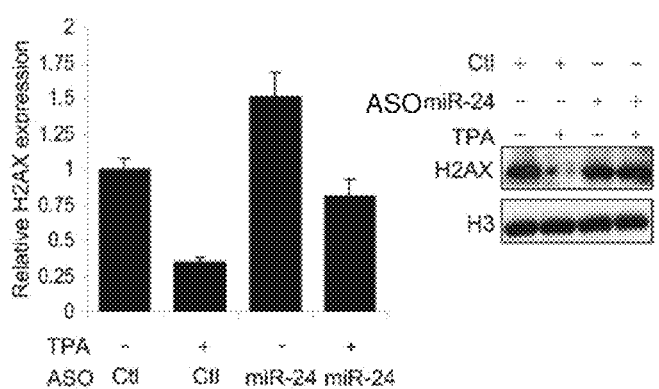
Figure 7C:
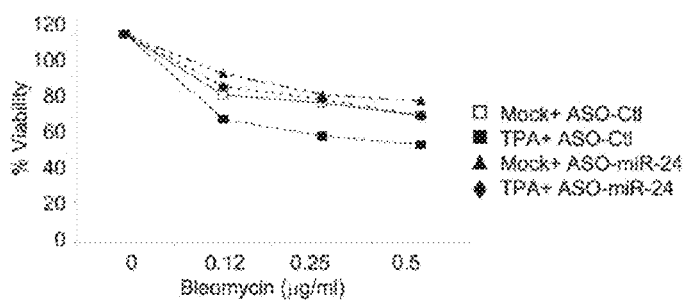
Figure 7D:
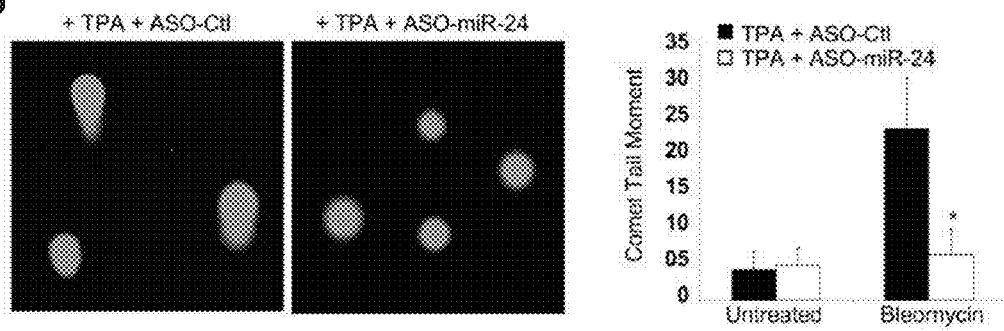
Figure 8A:
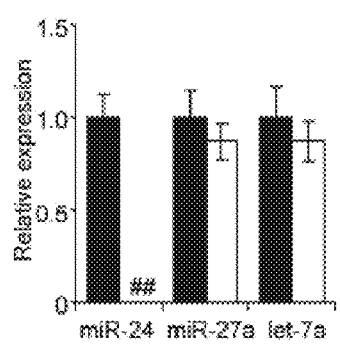
FIG. 8A shows that miR-24 knockdown in K562 cells specifically decreases miR-24 levels, assayed by qRT-PCR in cells transfected with miR-24 ASO (white) relative to control ASO (black). Expression relative to U6 snRNA is depicted normalized to control cells.
Figure 8B:
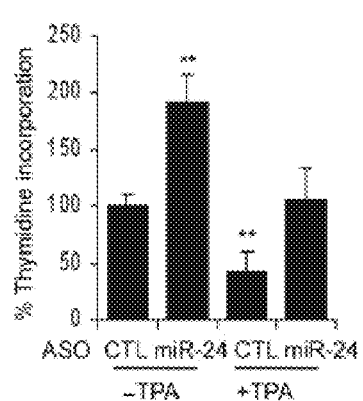
FIG. 8B shows that miR-24 knockdown with ASO increases K562 cell proliferation measured by thymidine uptake, both in the presence and absence of TPA. The decline in proliferation with TPA is completely restored by antagonizing miR-24.
Figure 8C:
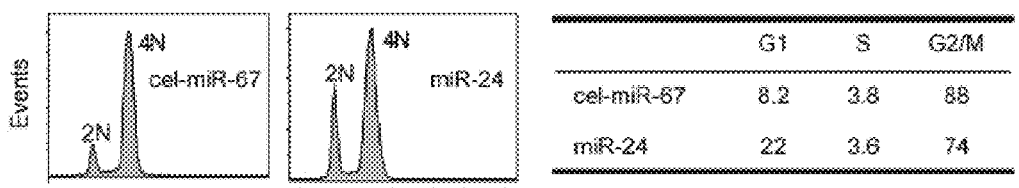
FIG. 8C shows that miR-24 over-expression increases the G1 compartment in HepG2 cells. HepG2 cells transfected with miR-24 or control mimic for 48 hr were stained with propidium iodide and analyzed by flow cytometry. Representative analysis of three independent experiments is shown. Error bars represent standard deviation from 3 independent experiments (FIG. 8A to FIG. 8C). *, p<0.05; **, p<0.01; #, p<0.005.
Figure 9A:
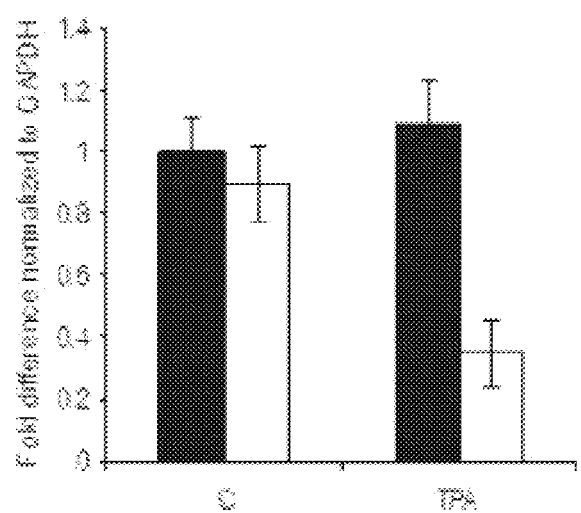
FIG. 9A shows H2AX mRNA analyzed by qRT-PCR using coding region primers decreases ~4-fold during TPA induced differentiation of K562 cells. These primers amplify both H2AX transcripts. GAPDH mRNA was used for normalization.
Figure 9B:
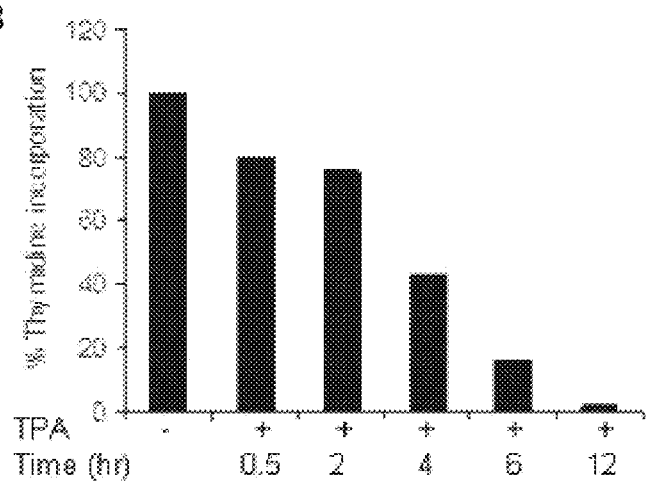
FIG. 9B shows kinetics of thymidine incorporation in TPA-treated K562 cells. By 12 h there is no thymidine incorporation, indicating that cells have stopped dividing.
Figure 10A:
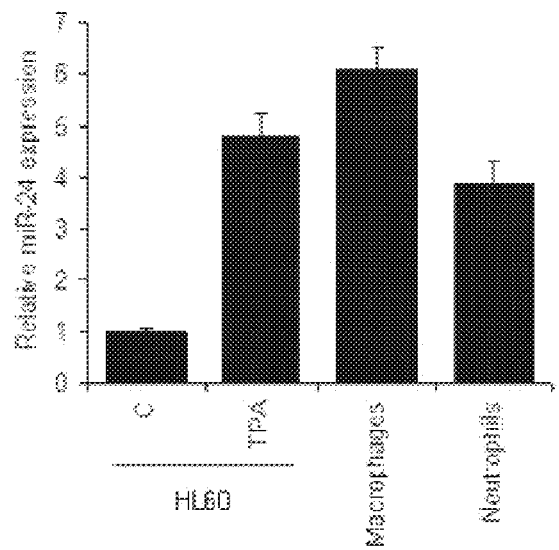
FIG. 10A and FIG. 10B show that miR-24 levels and H2AX levels in primary human peripheral blood macrophages and granulocytes are comparable to cells generated by in vitro differentiation.
Figure 10B:
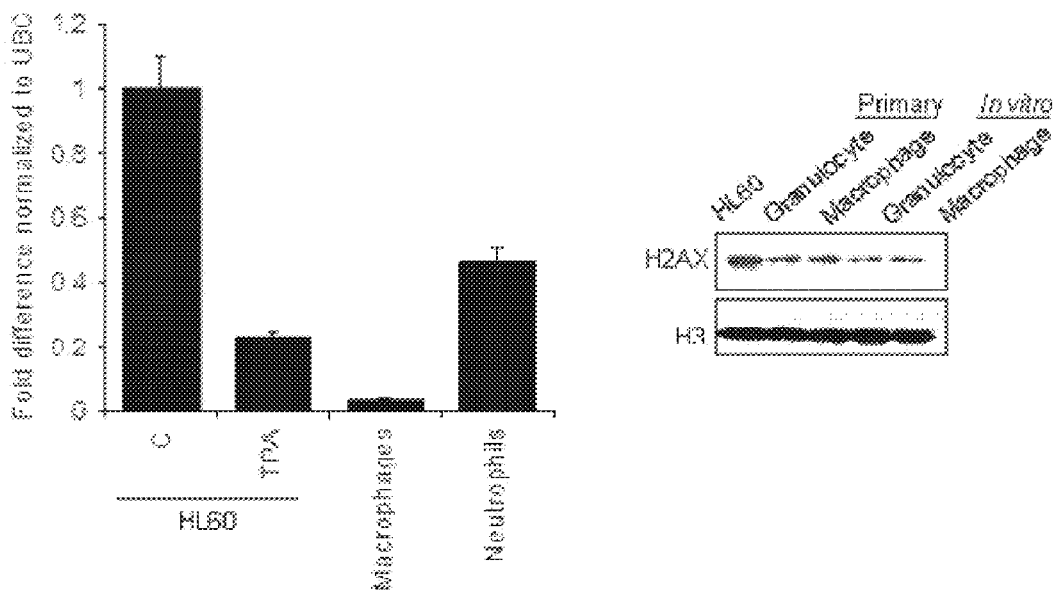
Figure 11:
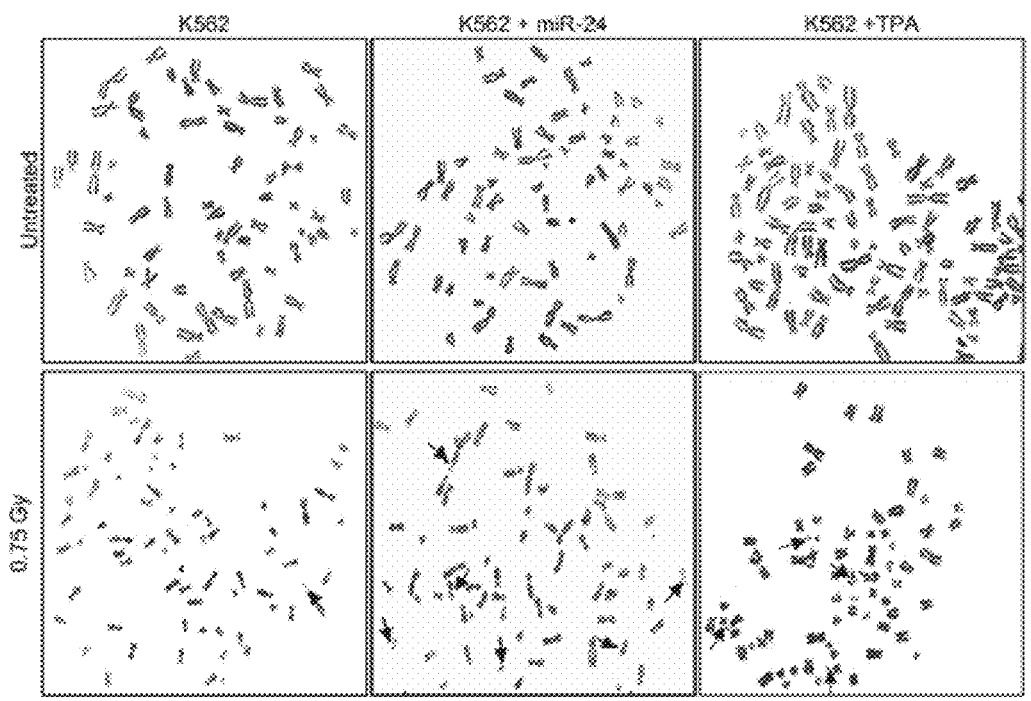
FIG. 11 shows that representative images of metaphase chromosome spreads were prepared from treated cells 24 h after γ-irradiation. Arrows mark chromosome breaks or fragments.
Figure 12:
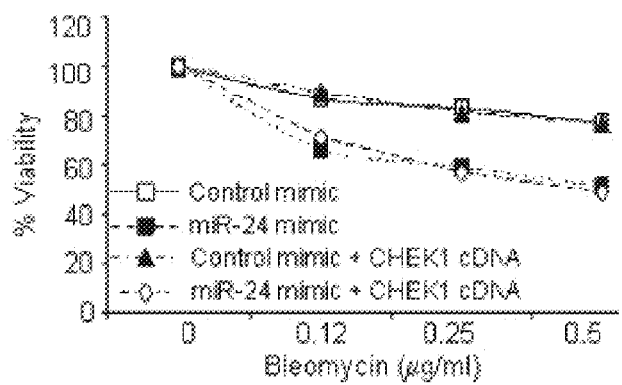
FIG. 12 shows that miR-24-mediated hypersensitivity of K562 cells to bleomycin is not rescued by expression of miR-24-insensitive CHEK1. Cells were mock transfected or transfected with miR-24 mimic and/or CHEK1 cDNA lacking the 3'UTR. Cell viability was assayed 2 d after exposure to DNA damage and depicted relative to that of undamaged cells. Immunoblot demonstrates miR-24-mediated decrease in CHEK1 protein and its restoration by transfecting CHEK1 cDNA lacking the 3'UTR.
Figure 13:
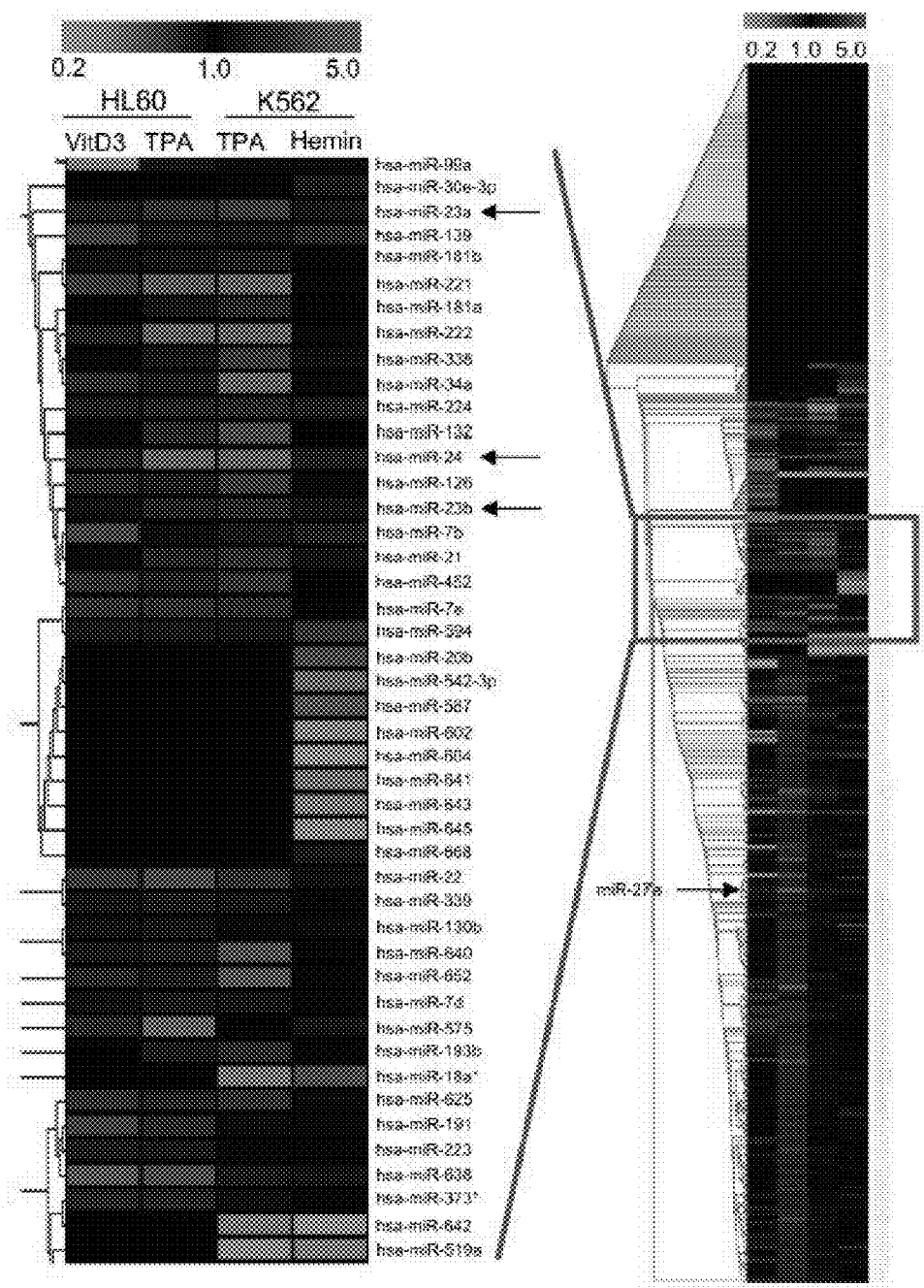

We next tested the effect of inhibiting miR-24 on sensitivity to genotoxic stress. When K562 cells were transfected with miR-24 antisense oligonucleotides (ASO), miR-24 expression was reduced even during TPA differentiation (FIG. 7A). The reduction in miR-24, which correlated with enhanced H2AX mRNA and protein (FIG. 7B), had no effect on undifferentiated K562 cells, but significantly reduced sensitivity to bleomycin in differentiated cells (FIG. 7C).

Why is there a mechanism to dampen DSB repair in terminally differentiated cells? One explanation is that most DSBs are generated during DNA replication and this mode of regulation allows differentiated cells to economize and conserve cellular resources under stress-free conditions. Another possibility is that suppression of repair triggers apoptosis, and this may be preferred to error prone repair via NHEJ (the primary mode of DSB repair in these cells), which would result in viable, but malfunctioning, cells. Although this solution makes sense for regenerating cells, such as hematopoietic cells and myocytes, it might not be a good solution for long-lived terminally differentiated cells, like neurons, with poor regenerative capacity. It will be worthwhile to determine whether miR-24 is up-regulated during terminal differentiation of all cell types or only in lineages that are continuously renewing. It is noteworthy that at least one miR-24 cluster has been reported to be deleted in some poor prognosis cases of CLL (19), a leukemia known to dysregulate key anti-apoptotic genes. Based on our findings here, inappropriate under-expression of miR-24 would be predicted to enhance DNA repair and thereby enhance resistance to cytotoxic cancer therapies.

This study focused on the effect of miR-24 on H2AX and DSB repair. Both H2AX mRNA and protein are reduced by miR-24 expression. miR-24 is likely operating predominantly by inhibiting translation since the effect on protein levels is much greater than on mRNA. Other proteins recruited to DSB and required for their repair are BRCA1, PCNA and CHEK1, whose transcripts both precipitate with miR-24 and show protein down-regulation upon miR-24 over-expression (accompanying patent application U.S. Ser. No. 61/098,696, filed on Sep. 19, 2008). BRCA1 and PCNA are important in repairing DNA replication-mediated breaks by HR and CHEK1 arrests dividing cells in response to DNA damage. However, H2AX is required for DSB repair without bias for dividing or non-dividing cells—it is important for both HR (active only in dividing cells) and NHEJ (throughout the cell cycle) (20). The observation that DSB repair was completely restored by over-expressing H2AX in differentiating cells, or cells over-expressing exogenous miR-24, suggests that the key target of miR-24 in DSB repair is H2AX.

REFERENCES

S1. P. S. Moorhead, P. C. Nowell, W. J. Mellman, D. M. Battips, D. A. Hungerford, *Exp Cell Res* 20, 613 (1960).
1. T. Nouspikel, P. C. Hanawalt, *DNA Repair (Amst)* 1, 59 (2002).
2. C. Lukas et al., *Cancer Res* 61, 4990 (2001).
3. P. L. Puri, V. Sartorelli, *J Cell Physiol* 185, 155 (2000).
4. L. Belloni et al., *Oncogene* 25, 3606 (2006).
5. M. Yaneva, S. Jhiang, *Biochim Biophys Acta* 1090, 181 (1991).
6. J. R. Neilson, G. X. Zheng, C. B. Burge, P. A. Sharp, *Genes Dev* 21, 578 (2007).
7. Q. Sun et al., *Nucleic Acids Res* 36, 2690 (2008).
8. G. L. Moldovan, B. Pfander, S. Jentsch, *Cell* 129, 665 (2007).
9. Kramer, J. Lukas, J. Bartek, *Cell Cycle* 3, 1390 (2004).
10. Y. Liu, H. I. Kao, R. A. Bambara, *Annu Rev Biochem* 73, 589 (2004).
11. B. Kavli, M. Otterlei, G. Slupphaug, H. E. Krokan, *DNA Repair (Amst)* 6, 505 (2007).
12. P. T. Tran, N. Erdeniz, L. S. Symington, R. M. Liskay, *DNA Repair (Amst)* 3, 1549 (2004).

13. O. Fernandez-Capetillo, A. Lee, M. Nussenzweig, A. Nussenzweig, *DNA Repair (Amst)* 3, 959 (2004).
14. D. Acosta-Alvear et al., *Mol Cell* 27, 53 (2007).
15. J. H. Petrini, T. H. Stracker, *Trends Cell Biol* 13, 458 (2003).
16. M. Stucki, S. P. Jackson, *DNA Repair (Amst)* 5, 534 (2006).
17. C. H. Bassing et al., *Cell* 114, 359 (2003).
18. Celeste et al., *Cell* 114, 371 (2003).
19. G. A. Calin et al., *Proc Nall Acad Sci USA* 101, 11755 (2004).
20. M. Shrivastav, L. P. De Haro, J. A. Nickoloff, *Cell Res* 18, 134 (2008).
21. Pillai, R. S., Bhattacharyya, S. N. & Filipowicz, W. *Trends Cell Biol.* 17, 118-126 (2007).
22. Ambros, V. *Nature* 431, 350-355 (2004).
23. Bartel, D. P. *Cell* 116, 281-297 (2004).
24. Sevignani, C., Calin, G. A., Siracusa, L. D. & Croce, C. M. *Mamm. Genome* 17, 189-202 (2006).
25. Tzur, G. et al. *PLoS ONE* 3, e3726 (2008).
26. Bartel, D. P. *Cell* 136, 215-233 (2009).
27. Mannironi, C., Bonner, W. M. & Hatch, C. L. *Nucleic Acids Res.* 17, 9113-9126 (1989).
28. Sandberg, R., Neilson, J. R., Sarma, A., Sharp, P. A. & Burge, C. B. *Science* 320, 1643-1647 (2008).
29. Song, E. et al. *J. Virol.* 77, 7174-7181 (2003).
30. Barad, O. et al. *Genome Res.* 14, 2486-2494 (2004).
31. Moorhead, P. S., Nowell, P. C., Mellman, W. J., Battips, D. M. & Hungerford, D. A. *Exp. Cell Res.* 20, 613-616 (1960).

EQUIVALENTS

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A method comprising steps of:
   administering to an individual who is suffering from or susceptible to a cell proliferative disorder a composition comprising an miR-24 agent in an amount sufficient to inhibit cell proliferation in combination with a DNA damage agent and/or cell proliferation disorder treatment method that produces DNA double-strand breaks,
   isolating cells from the individual administered the miR-24 agent and preparing Wright-stained metaphase chromosome spreads from the isolated cells or staining the isolated cells from the individual with SYBR Green and performing single cell gel electrophoresis on the isolated cells, thereby measuring DNA damage and detecting DNA damage repair to be reduced in the isolated cells, as compared to control cells, thereby identifying the individual administered the miR-24 agent to possess reduced DNA damage repair,
   further comprising administering to the individual so identified to possess reduced DNA damage repair the miR-24 agent and γ-irradiation or a genotoxic drug.

2. A method comprising steps of:
   administering to an individual who is suffering from or susceptible to a cell proliferative disorder a composition comprising an miR-24 agent in an amount sufficient to render cells of the individual hypersensitive to a DNA damage agent and/or cell proliferation disorder treatment method that produces DNA double-strand breaks,
   isolating cells from the individual administered the miR-24 agent and preparing Wright-stained metaphase chromosome spreads from the isolated cells or staining the isolated cells from the individual with SYBR Green and performing single cell gel electrophoresis on the isolated cells, thereby measuring DNA damage and detecting DNA damage repair to be reduced in the isolated cells, as compared to control cells, thereby identifying the individual administered the miR-24 agent to possess reduced DNA damage repair,
   further comprising administering to the individual so identified to possess reduced DNA damage repair the miR-24 agent and γ-irradiation or a genotoxic drug.

3. The method of claim 1, wherein the amount is an amount sufficient to suppress levels and/or activity of one or more DNA repair proteins.

4. The method of claim 2, wherein the DNA repair proteins are selected from the group consisting of photolyases, methyltransferases, AP endonucleases, exonucleases, histone variants, transcription factors that regulate expression of DNA repair genes, and DNA glycosylases, and combinations thereof.

5. The method of claim 1, wherein the step of administering comprises administering in combination with other cell proliferation disorder treatment methods and/or therapeutic agents.

6. The method of claim 2, wherein the amount is an amount sufficient to suppress levels and/or activity of one or more DNA repair proteins.

7. The method of claim 2, wherein the step of administering comprises administering in combination with other cell proliferation disorder treatment methods and/or therapeutic agents.

8. The method of claim 1 or 2, wherein the cell proliferative disorder is a hematopoietic cell proliferative disorder.

9. A method comprising steps of:
   administering to an individual who is suffering from or susceptible to a cell proliferative disorder a composition comprising an miR-24 agent in an amount sufficient to down-regulate the expression of H2AFX, and thereby inhibit cell proliferation,
   wherein the miR-24 agent is administered in combination with a DNA damage agent and/or cell proliferation disorder treatment method that produces DNA double-strand breaks,
   isolating cells from the individual administered the miR-24 agent, preparing cDNA from the isolated cells and performing quantitative RT-PCR on the cDNA using primers from the H2AX coding region and SYBR Green, thereby measuring H2AFX expression and detecting H2AFX expression to be reduced in the isolated cells, as compared to control cells, thereby identifying the individual administered the miR-24 agent to possess reduced H2AFX expression,
   further comprising administering to the individual so identified to possess reduced H2AFX expression the miR-24 agent and γ-irradiation or a genotoxic drug.

* * * * *

SEQUENCE LISTING

<160> NUMBER OF SEQ ID NOS: 15

<210> SEQ ID NO 1
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 1
uggcucaguu cagcaggaac ag                                              22

<210> SEQ ID NO 2
<211> LENGTH: 21
<212> TYPE: RNA

```
<213> ORGANISM: Artificial Sequence
<220> FEATURE:
<223> OTHER INFORMATION: Synthetic oligonucleotide

<400> SEQUENCE: 2
cucauggaaa gagcugagcc g                                              21

<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
cccugucugg acugagccu                                                 19

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tgcaccacca actgcttagc                                                20

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ggcatggact gtggtcatga g                                              21

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
atttgggtcg cggttcttg                                                 19

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
tgccttgaca ttctcgatgg t                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
agcaaactca actcggcaat                                                20
```

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
actccccaat gcctaaggtt                                                   20

<210> SEQ ID NO 10
<211> LENGTH: 18
<212> TYPE: DNA
<213> ORGANISM: Artificial Sequence
<220> FEATURE:
<223> OTHER INFORMATION: Synthetic primer

<400> SEQUENCE: 10
ggcctccagt tcccagtg                                                     18

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tcagcggtga ggtactccag                                                   20

<210> SEQ ID NO 12
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 12
ucauggaaag agcugagcc                                                    19

<210> SEQ ID NO 13
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 13
ucauggaaag aggauuagg                                                    19

<210> SEQ ID NO 14
<211> LENGTH: 17
<212> TYPE: RNA
<213> ORGANISM: Artificial Sequence
<220> FEATURE:
<223> OTHER INFORMATION: Synthetic oligonucleotide

<400> SEQUENCE: 14
ccugucugga cugagcc                                                      17

<210> SEQ ID NO 15
<211> LENGTH: 17
<212> TYPE: RNA
<213> ORGANISM: Artificial Sequence
<220> FEATURE:

```
<223> OTHER INFORMATION: Synthetic oligonucleotide

<400> SEQUENCE: 15
ccugucugga gauuagg                                                    17
```